United States Patent [19]
Lampropoulos et al.

[11] Patent Number: 5,817,072
[45] Date of Patent: *Oct. 6, 1998

[54] CENTRAL VENOUS SYSTEM CATHETER APPARATUS WITH MEANS FOR SUBCUTANEOUS DELIVERY OF ANESTHETIC AGENT OF OTHER FLUID MEDICAMENT

[75] Inventors: Fred P. Lampropoulos, Sandy; Jim Mottola; Ron Stoker, both of South Jordan, all of Utah

[73] Assignee: Merit Medical Systems, Inc., South Jordan, Utah

[*] Notice: The term of this patent shall not extend beyond the expiration date of Pat. No. 5,405,334.

[21] Appl. No.: 832,043

[22] Filed: Apr. 2, 1997

Related U.S. Application Data

[63] Continuation-in-part of Ser. No. 621,017, Mar. 22, 1996, Pat. No. 5,665,076, which is a continuation of Ser. No. 417,824, Apr. 6, 1995, Pat. No. 5,533,986, which is a continuation-in-part of Ser. No. 198,625, Feb. 18, 1994, Pat. No. 5,405,334.

[51] Int. Cl.[6] ............................................. A61M 5/00
[52] U.S. Cl. ...................................................... 604/264
[58] Field of Search ................................ 604/164, 264, 604/280–284, 53

[56] References Cited

U.S. PATENT DOCUMENTS

| | | | |
|---|---|---|---|
| 1,968,997 | 8/1934 | Drucker | 174/177 |
| 3,670,729 | 6/1972 | Bennett et al. | 128/214.4 |
| 4,149,535 | 4/1979 | Volder | 128/214.4 |
| 4,306,562 | 12/1981 | Osborne | 128/348 |
| 4,391,029 | 7/1983 | Czuba et al. | 29/450 |
| 4,581,019 | 4/1986 | Curelaru et al. | 604/164 |
| 4,865,593 | 9/1989 | Ogawa et al. | 604/264 |
| 5,125,904 | 6/1992 | Lee | 604/164 |
| 5,147,334 | 9/1992 | Moss | 604/264 |
| 5,158,553 | 10/1992 | Berry et al. | 604/248 |
| 5,178,611 | 1/1993 | Roseberg | 604/172 |
| 5,207,655 | 5/1993 | Sheridan | 604/247 |
| 5,250,038 | 10/1993 | Melder et al. | 604/264 |
| 5,254,104 | 10/1993 | Furlow et al. | 604/264 |
| 5,267,996 | 12/1993 | Paul | 604/167 |
| 5,269,755 | 12/1993 | Bodicky | 604/53 |
| 5,282,785 | 2/1994 | Shapland et al. | 604/23 |
| 5,300,032 | 4/1994 | Hibbs et al. | 604/164 |
| 5,324,276 | 6/1994 | Rosenberg | 604/269 |
| 5,330,449 | 7/1994 | Prichard et al. | 604/282 |
| 5,354,271 | 10/1994 | Voda | 604/49 |
| 5,405,334 | 4/1995 | Roth et al. | 604/264 |
| 5,533,986 | 7/1996 | Mottola et al | 604/264 |

OTHER PUBLICATIONS

Lambert et al., "New Vascular Sheath for Subcutaneous Drug Administration: Design, Animal Testing, and Clinical Application for Pain Prevention After Angioplasty." *Catheterization and Cardiovascular Diagnosis*, 37, pp. 68–72 (1996).

*Primary Examiner*—Manuel Mendez
*Attorney, Agent, or Firm*—Workman, Nydegger, & Seeley

[57] ABSTRACT

An indwelling catheter apparatus for providing fluid to the central venous system, comprising: (a) an indwelling cannula adapted for insertion into subcutaneous tissue in the chest wall and approximately within the superior vena cava, the indwelling cannula having (i) an indwelling distal end, the distal end having an exit port in fluid communication with the superior vena cava; (ii) a proximal hub end adapted for positioning outside of the body; and (iii) a primary lumen for delivering fluid to the circulatory system; and (b) delivery means for delivering fluid medicament to the subcutaneous tissue surrounding a portion of the cannula.

21 Claims, 17 Drawing Sheets

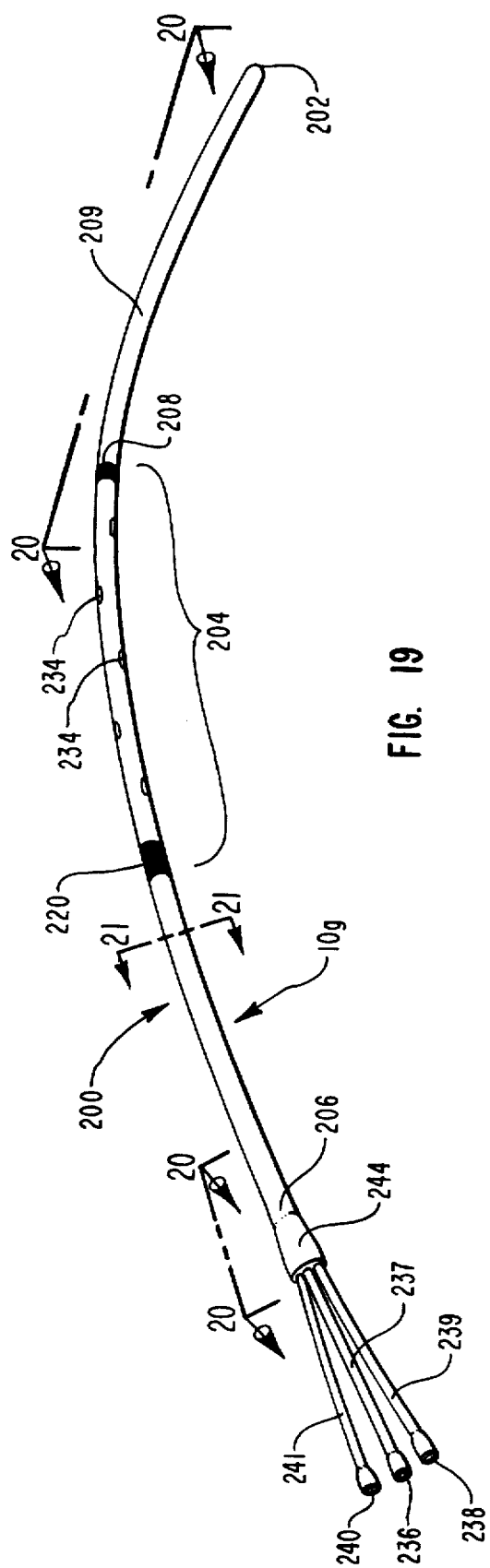
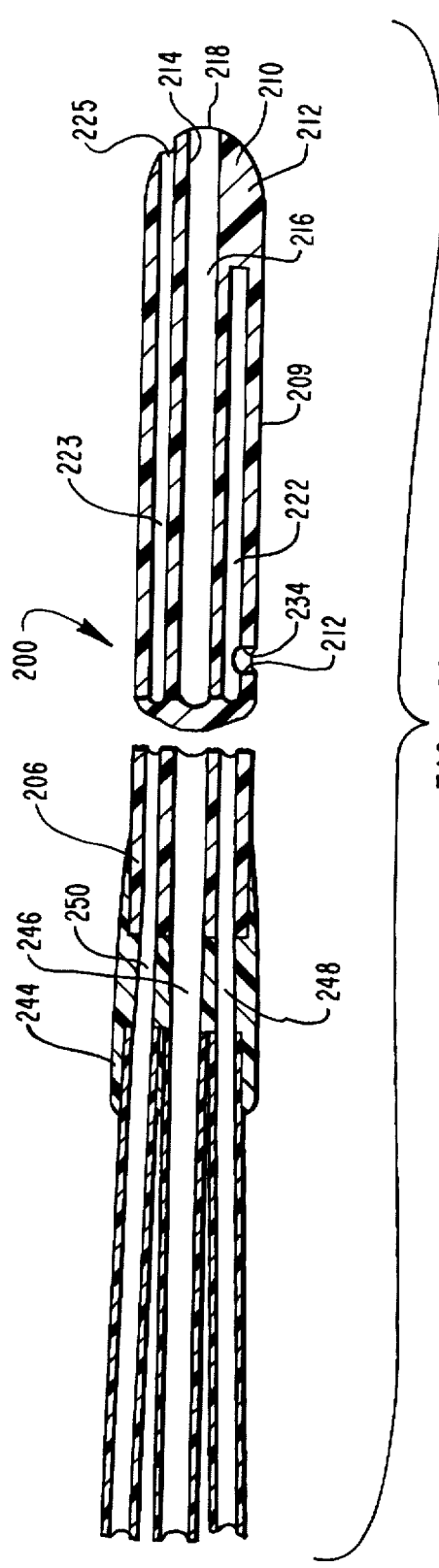
FIG. 19
FIG. 20

CENTRAL VENOUS SYSTEM CATHETER APPARATUS WITH MEANS FOR SUBCUTANEOUS DELIVERY OF ANESTHETIC AGENT OF OTHER FLUID MEDICAMENT

RELATED APPLICATION INFORMATION

This application is a continuation-in-part of U.S. patent application Ser. No. 08/621,017 filed Mar. 22, 1996, now U.S. Pat. No. 5,665,076, which is a continuation of U.S. patent application Ser. No. 08/417,824, filed Apr. 6, 1995, and issued on Jul. 9, 1996 as U.S. Pat. No. 5,533,986, which is a continuation-in-part of U.S. patent application Ser. No. 08/198,625, filed on Feb. 18, 1994, and issued as U.S. Pat. No. 5,405,334 on Apr. 11, 1994, each of which are incorporated herein by reference.

BACKGROUND OF THE INVENTION

1. Field of the Invention

This invention relates to a catheter apparatus with a means for subcutaneous delivery of anesthetic agents or other fluid medicaments, and more particularly to a central venous system catheter apparatus having subcutaneous infusion ports that provide for the administration of a local anesthesia or other medicaments to subcutaneous tissue.

2. The Present State of the Art

Catheter devices are widely used for a variety of medical applications. Generally, a catheter is a hollow, tubular cannula that is capable of being inserted into canals, vessels, passageways, or other body cavities so as to permit injection or withdrawal of fluids, or to keep a passage open.

Some catheters provide fluid into a patient's central venous system for long term therapy, such as chemotherapy or antibiotic therapy. Typically, a distal portion of the catheter is inserted approximately within the superior vena cava while a relatively proximal portion of the catheter is disposed through and remains within the chest wall. These central venous system catheters include an infusion port at a proximal end which extends out of the body for the continual introduction of fluid into the catheter and an exit port at a distal end to be disposed approximately within the superior vena cava for delivery of the fluid into the patient's circulatory system.

Also, by way of example, some catheter devices are used for controlling, directing and placing medical devices, such as intubation tubes or dilation catheters, into a body cavity, such as the trachea, a blood vessel, or the heart. These types of insertion catheters are commonly referred to as intubators, insertion sheaths, and/or dilators.

Given that catheters are used for such a wide variety of applications, catheters are implemented in a variety of designs, shapes and sizes. However, when used, almost all catheters share the universal characteristic of having to be passed through the skin and subcutaneous tissue of the patient so as to be inserted into the proper body cavity.

Depending on the medical procedure, the catheter is very often left in the body cavity over a relatively long period of time. As such, the skin and subcutaneous tissue through which the catheter device is inserted often becomes very swollen and tender, and thus extremely sensitive. Consequently, when the catheter is eventually retracted from the patient, the patient will often experience great discomfort. This discomfort may agitate the patient and thereby hinder the ability of medical personnel to effectively retract the catheter and/or treat the patient.

For example, in a percutaneous transluminal coronary angioplasty (PTCA) procedure, a patient is administered a local anesthesia and an intravascular sheath introducer (a type of catheter device) is inserted through the patient's skin in the groin area and into the femoral artery. In so doing, the sheath introducer necessarily passes through the area of subcutaneous tissue that lies between the skin and the femoral artery. Once inserted, the sheath introducer catheter provides a means for introducing the dilation catheter for performing the PTCA procedure.

Following the PTCA procedure, the sheath introducer is usually left within the femoral artery for a period ranging between four to twenty-four hours. Typically, the sheath is left in place because blood thinning drugs, such as Heparin, are administered to the patient. The effects of such drugs must wear off before the sheath can be removed in order to avoid hemorrhaging problems. Similarly, the device may be left in the patient as a precaution, in case quick access to the femoral artery is needed due to subsequent complications, such as an abrupt closure of the artery. In any event, by the time the sheath is retracted, the patient's skin and subcutaneous tissue through which the catheter is inserted is typically very swollen, bruised and tender. Also, by this time, the numbing effects of the earlier administered local anesthesia have completely worn off. Consequently, as the sheath is retracted from the femoral artery, the subcutaneous tissue and the overlying skin, the patient can experience considerable pain.

Also by way of example, central venous system catheters are typically designed so that a distal portion thereof remains within a vein, typically the jugular or subclavian vein, such that the distal end is located approximately within the superior vena cava. To secure the catheter in place and to allow for continual fluid delivery to the circulatory system, a portion of the catheter is often disposed through and remains within a stoma in the chest wall for a prolonged period of time. The proximal end of the catheter protrudes from the chest wall, typically medial to the nipple. At least one fluid entrance port is coupled to the proximal end of the catheter for prolonged delivery of fluid to the catheter.

The prolonged retention of the central venous system catheter within the stoma can cause infection, swelling, and pain. In addition, movement of the catheter within the stoma or removal of the catheter from the stoma can cause considerable pain.

Pain experienced during removal is known to occasionally cause vasovagal syncope type reactions, which can potentially result in a variety of undesirable patient responses—including a drop in blood pressure and heart rate. This can be hazardous when it occurs so soon after a medical procedure, and may thus require treatment with intravenous Atropine, or other drugs. Pain may also cause the patient to become agitated, which makes it difficult for medical personnel to properly administer arterial compression. This can lead to a hematoma formation within the subcutaneous tissue adjacent to the catheter.

Although medical personnel can administer a local anesthesia to the area, this must be done with a hypodermic needle, which usually causes as much discomfort or pain as the actual retraction of the catheter device. Thus, there is not a medical device available which adequately relieves a patient's discomfort during catheter retraction, and there is a need to be able to administer a local anesthesia to the subcutaneous tissue surrounding a catheter device prior to the retraction of the device, in a relatively painless and easy manner.

BRIEF SUMMARY AND OBJECTS OF THE INVENTION

The apparatus of the present invention has been developed in response to the present state of the art. Thus, it is an overall object of the present invention to provide an apparatus which provides for the ability to painlessly administer local anesthesia or other medicaments to an area of subcutaneous tissue through which a catheter device has been inserted.

A further object of the present invention is to provide an apparatus that permits subcutaneous delivery of such medicaments but which also prevents bodily fluids from entering the apparatus while it is inserted and remains within the patient's body.

Yet another important object of the present invention is to provide an anesthetizing catheter sheath apparatus that can be manufactured either as an integral part of a catheter device, or as an apparatus that can be detachably mounted to a catheter device.

Yet another important object of the present invention is to provide a central venous system catheter having delivery means for delivering fluid medicant to essentially only the area of subcutaneous tissue surrounding the catheter.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

Briefly summarized, the foregoing and other objects are achieved with a catheter apparatus that is inserted into a patient's body through subcutaneous tissue. In one presently preferred embodiment, a sheath fits over the catheter and is designed for insertion together with the catheter through the subcutaneous tissue. Once the catheter device is inserted into the patient's body, the outer surface of the catheter device necessarily passes through the patient's skin and a portion of underlying, subcutaneous tissue. The sheath which is disposed on the outer surface of the catheter device is also thus inserted through the subcutaneous tissue. Prior to retracting the catheter device, medical personnel can administer an anesthetic agent by infusing it into the surrounding subcutaneous tissue from the anesthetizing sheath. In this way, the subcutaneous tissue will be numbed, and the patient will experience no pain while the catheter device is retracted. In addition to anesthetic agents, the sheath can also be used to deliver a wide variety of other types of fluid medicaments to the subcutaneous tissue. For instance, the sheath may be used to deliver topical antibacterial agents to the tissue.

In one presently preferred embodiment of the present invention, the anesthetizing sheath apparatus can be permanently mounted to the catheter device, and is thus manufactured as an integral part of the catheter device.

In another presently preferred embodiment of the present invention, the anesthetizing sheath can be detachably mounted to the outer surface of the catheter device. In this manner, the anesthetizing sheath can be designed for use with any of a wide variety of existing catheter devices already on the market, thereby increasing its versatility.

In a still further embodiment of the invention, rather than using a sheath, the outer wall of the catheter device is provided with a secondary lumen, into which the anesthetic agent is injected and from which the anesthetic agent is infused into surrounding subcutaneous tissue.

In yet another embodiment of the invention, an indwelling catheter apparatus is provided for delivery of fluid to a patient's central venous system. The catheter apparatus comprises an indwelling cannula adapted typically for insertion through a patient's chest wall and approximately within the patient's superior vena cava. The indwelling cannula has (i) an indwelling distal end having an exit port disposed approximately within the superior vena cava, and (ii) a proximal hub end and adapted for positioning outside of the body.

The catheter apparatus further comprises delivery means for delivering fluid medicament to essentially only the area of subcutaneous tissue of the chest wall surrounding the cannula. The delivery means includes means for communicating fluid medicament to essentially only the area of subcutaneous tissue surrounding the cannula. The central venous system catheter apparatus may also be employed in other areas of the body to deliver fluid to the circulatory system.

BRIEF DESCRIPTION OF THE DRAWINGS

In order to more fully understand the manner in which the above-recited and other advantages and objects of the invention are obtained, a more particular description of the invention will be rendered by reference to specific embodiments thereof which are illustrated in the appended drawings. Understanding that these drawings depict only typical embodiments of the invention and are therefore not to be considered limiting of its scope, the invention in its presently understood best mode for making and using the same will be described with additional specificity and detail through the use of the accompanying drawings in which:

FIG. 19 is a perspective view of an indwelling catheter apparatus for providing fluid to a patient's circulatory system.

FIG. 20 is a cross-sectional, cut-away view of the catheter apparatus of FIG. 19.

DETAILED DESCRIPTION OF THE PREFERRED EMBODIMENTS

Figure 1:
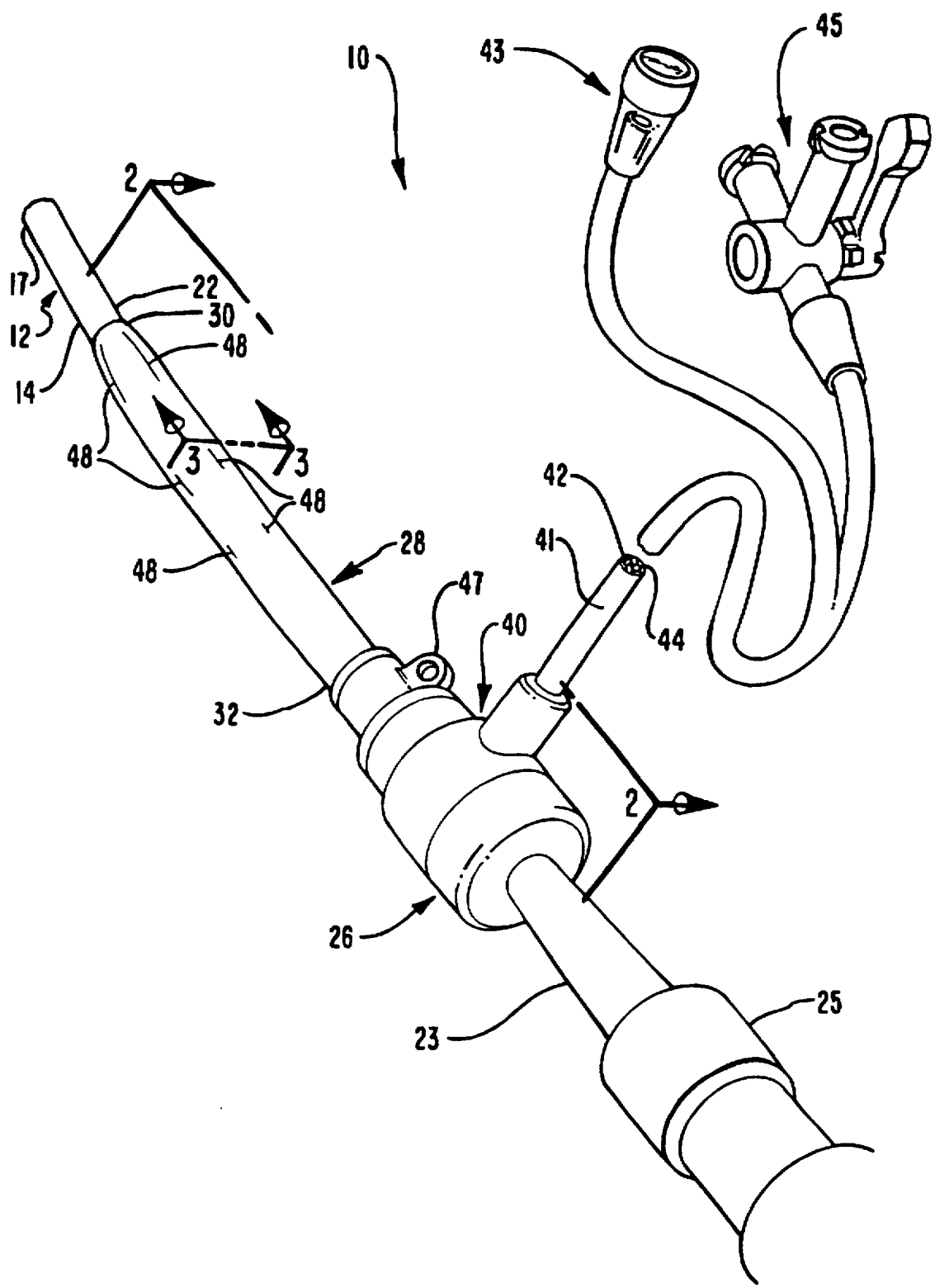
FIG. 1 is a perspective view illustrating one presently preferred embodiment of the catheter apparatus of the present invention.

Reference is next made to the drawings, wherein like parts are designated with like numerals throughout. Referring first to FIG. 1, one presently preferred embodiment of the invention is illustrated. FIG. 1 represents a perspective view of the catheter apparatus of the present invention, designated generally at 10. Catheter apparatus 10 includes a catheter means, as for example a catheter device designated generally at 12, for insertion through subcutaneous tissue. As used herein, the term catheter device is intended to broadly cover the general category of cannula-type devices referred to as catheters. Thus the term catheter device is intended to refer to any hollow, tubular cannula-type device that is capable of being inserted into canals, vessels, passageways, or other body cavities so as to permit injection or withdrawal of fluids, or to keep a passage open. Further, the term is intended to include insertion devices which are used for controlling, directing and placing medical devices, such as intubation tubes or dilation catheters, into a body cavity, such as the trachea, a blood vessel, or the heart, and which are commonly referred to as intubators, insertion sheaths, and/or dilators.

For purposes of example, the catheter device 12 illustrated in FIG. 1 is an insertion sheath comprised of an indwelling cannula 14 which is adapted for insertion through subcutaneous tissue and into a patient's body. As is better shown in FIG. 2, the cannula 14 is inserted into a patient's body (typically via a guide wire while the patient is numbed with a local anesthetic) so as to have a distal end 17 disposed within a body cavity, such as a blood vessel 16. As is shown, the cannula 14 necessarily passes through the patient's skin layer 18 and the area of subcutaneous tissue 20 that lies between the skin layer 18 and the body cavity, such as the blood vessel 16. Thus, once the cannula 14 is properly positioned, a portion 22 of the cannula 14 remains disposed within the area of subcutaneous tissue 20.

Once in place, the insertion sheath cannula 14 is used for controlling and directing the placement of another medical device, as for example a dilation catheter 24 for use in a PTCA procedure. The dilation catheter 24 is inserted into the hollow cannula 14 via the proximal hub end 26 of the catheter device 12, and the tubing 23 and connector 25 attached thereto. The proximal hub end 26 remains positioned outside of the body. Upon completion of the PTCA (or related) procedure, the dilation catheter 24 is removed from the cannula 14 through the proximal hub end 26. Typically, the distal end portion 17 of the cannula 14 then remains positioned within the patient, sometimes for as long as twenty-four hours. At the end of this time period (by which time all numbing effects of the local anesthesia have worn off) the patient's skin 18 and subcutaneous tissue 20 are swollen and very sensitive, and retraction of the cannula 14 can be extremely painful.

Referring again to FIG. 1, the catheter apparatus 10 of the present invention further comprises a sheath means, as for example a hollow cylindrical sleeve generally designated at 28, for placement onto at least a portion of the cannula 14 at a point intermediate of the distal end 17 and the proximal hub end 26. As is better shown in FIG. 2, the cylindrical sleeve 28 is positioned on the cannula 14 so as to be disposed on the portion 22 of cannula 14 that is surrounded by subcutaneous tissue 20 when the cannula 14 is indwelling within the patient's body.

Figure 2:
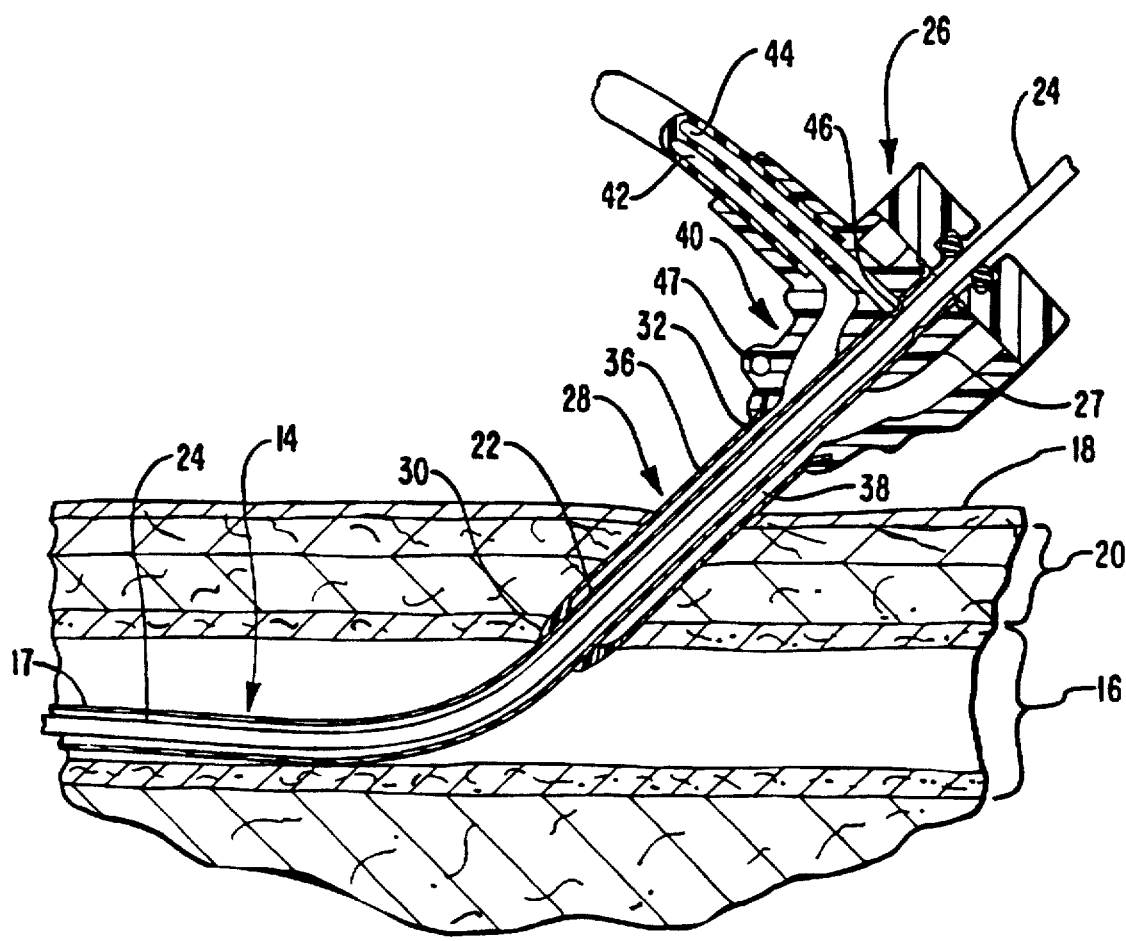
FIG. 2 is a cross-sectional view taken along line 2—2 in FIG. 1, and further illustrates the catheter apparatus of FIG. 1 disposed within a portion of a patient's body.
Figure 3:
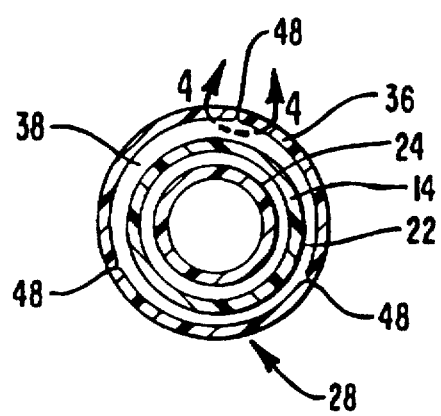
FIG. 3 is a cross-sectional view taken along line 3—3 in FIG. 1.

As is shown in the preferred embodiment of FIGS. 1 and 2, the cylindrical sleeve 28 has a distal end 30 and a proximal end 32. The cross-sectional view of FIG. 3 illustrates how hollow cylindrical sleeve 28 has an inner diameter which is greater than the outer diameter of cannula 14, and how cylindrical sleeve 28 is positioned on cannula 14 so as to be concentric with the cannula 14. Preferably, distal end 30 of cylindrical sleeve 28 is tapered where it terminates on the outer surface of cannula 14 so that the cylindrical sleeve 28 can be inserted with little or no trauma through the outer skin layer 18 and subcutaneous tissue 20. This tapered distal end 30 is best seen in FIG. 2.

The sheath means is further comprised of a means for sealing the sheath means in a fluid tight manner around the cannula 14 so as to prevent fluids, such as blood from the body, from escaping between the cannula 14 and the sheath means. In the embodiment of FIGS. 1 and 2, for example, this sealing function is accomplished by permanently affixing the cylindrical sleeve 28 over the outer surface 22 of the cannula 14. Thus, in this embodiment, the distal end 30 of the cylindrical sleeve 28 is fused, or otherwise suitably affixed, to the cannula 14. By so doing, fluids are prevented from entering the space or interior lumen 38 between the outer surface of the cannula 14 and the cylindrical sleeve 28.

The sheath means, as for example cylindrical sleeve 28, is further comprised of a means for delivering fluid medicament, such as an anesthetic agent (not shown), to essentially only that portion of subcutaneous tissue 20 that surrounds the sheath means. Delivery of fluid medicament is accomplished, for example, by way of the interior lumen 38 running from the distal end 30 to the proximal end 32 of the cylindrical sleeve 28. Delivery of fluid medicament is also aided by a hub means for delivering the fluid medicament to the interior lumen 38, and a plurality of valve means for communicating the fluid medicament from the interior lumen 38 to the subcutaneous tissue surrounding the sheath means.

By way of example, FIG. 2 illustrates cylindrical sleeve 28 as being comprised of a single cylindrical wall 36. In this particular embodiment, the interior lumen 38 is formed between the cylindrical wall 36 and the outer surface of the cannula 14. Interior lumen 38 is also shown in the cross-sectional view of FIG. 3.

By way of further example, FIGS. 1 and 2 illustrate how the hub means can be comprised of a hub 40 that is joined in a fluid tight manner to the proximal end 32 of the cylindrical sleeve 28, and to the proximal hub end 27 of the cannula 14. Hub 40 further comprises, for example, a first passageway means, such as a first hub lumen 42, for communicating the fluid medicament to the interior lumen 38. In addition, hub 40 comprises a second passageway means, such as second lumen 44, for providing fluid communication to the cannula 14 via a cannula access hole 46. FIG. 1 illustrates how the first and second hub lumens 42, 44 are preferably coupled to multi-lumen tube 41. Multi-lumen tube 41 is branched such that first hub lumen 42 is coupled to an infusion port 43, and second hub lumen is coupled to an I.V. valve assembly 45. In this way, a medical technician can administer fluid medicament with a syringe to the interior lumen 38 using infusion port 43.

By way of further example, FIG. 1 illustrates how the plurality of valve means are preferably comprised of a plurality of one way valve means spaced along the cylindrical sleeve 28. The one-way valve means not only allow the fluid medicament to be communicated from the interior lumen 38 to the subcutaneous tissue 20, but also act so as to prevent bodily fluids from entering the interior lumen 38. The one way valve function is provided by a plurality of one way slits 48 placed uniformly about the cylindrical sleeve 28. Because the width of the subcutaneous tissue 20 will vary from patient to patient, it is possible that the distal end 30 of the cylindrical sleeve 28, along with some of the slits 48, could be disposed within the blood vessel 16. In this situation, the one way slits 48 positioned within the portion of subcutaneous tissue 20 will properly communicate the anesthetic agent to the tissue 20, but any of the one way slits 48 that are located within the blood vessel 16 will prevent bodily fluids, such as blood, from entering the interior lumen 38.

As is further shown in FIG. 1, each slit 48 is preferably made longitudinally along the axis of the cylindrical sleeve 28. Slits 48 are uniformly located about the periphery of the cylindrical sleeve 28 so as to insure that the anesthetizing agent is evenly and uniformly delivered to the surrounding subcutaneous tissue 20. Further, the longitudinal length of each slit 48 changes depending on its location on the cylindrical sleeve 28. Preferably the slits 28 become progressively shorter as they near the proximal end 32 of the cylindrical sleeve 28. This variation in slit length is intended to help assure that fluid medicament is uniformly delivered from the proximal end 32 to the distal end 30 of sleeve 38. This may be especially important if one or more proximately located slits 48 are located outside of the patient's body during delivery of the fluid medicament.

Figure 4:
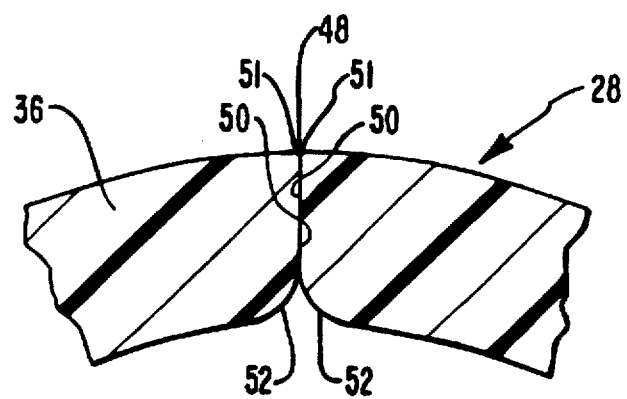
FIG. 4 is an enlarged cross-sectional view taken along line 4—4 of FIG. 3, showing a one way slit in a closed position.
Figure 5:
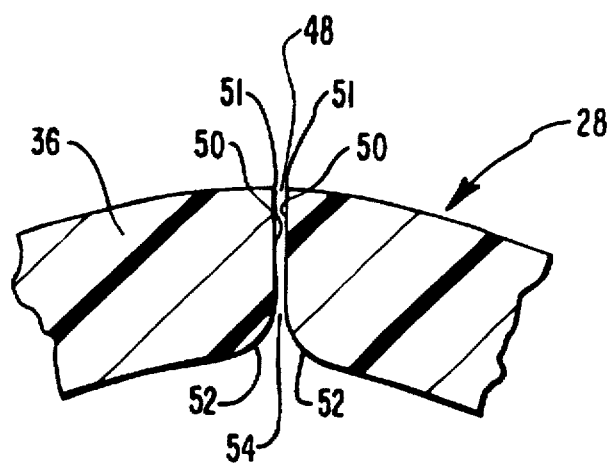
FIG. 5 is an enlarged cross-sectional view taken along line 4—4 of FIG. 3, showing a one way slit in an open position to permit infusion of anesthetic agent into surrounding subcutaneous tissue.

As is shown in FIGS. 3–5, each one way slit 48 extends completely through the cylindrical wall 36 of the cylindrical sleeve 28 so as to provide fluid communication with interior lumen 38. It is shown best in FIGS. 4 and 5 wherein each slit 48 is defined by opposed, aligned, normally abutting, parallel edges 50. FIG. 4 illustrates how a square portion 51 of the abutting edges 50 are normally engaged in a sealing relationship, and wherein the slit 48 is thereby in a closed position. The abutting edges 50 are further formed with rounded internal edge portions 52 that do not abut, but are spaced apart. In this closed position (shown in FIG. 4), the slit 48 will prevent any bodily fluids from entering the interior lumen 38.

Wall edges 50 are also capable of flexing outwardly from their closed position, responsive to a pressure generated within the interior lumen 38. In so doing, an orifice 54 is created, through which fluid such as the anesthetic agent, can flow. This open position is illustrated in FIG. 5. Thus, by applying a predetermined positive pressure to interior lumen 38, a fluid medicant such as an anesthetic agent is infused into the area of subcutaneous tissue 20 in which the cylindrical sleeve 28 is disposed, as shown in FIG. 2.

Slits 48 normally remain closed and wall edges 50 remain in an abutting position (FIG. 4). This requires that the cylindrical sleeve 28 have sufficient memory to return the slits 48 to the closed position after infusion of anesthetic agent is terminated. The cylindrical sleeve 28 may be constructed from a variety of materials with the required elasticity. Preferably, the cylindrical sleeve 28 is rigid enough to be easily inserted into the area of subcutaneous tissue 20 in conjunction with the cannula 14. At the same time, the cylindrical sleeve 28 should be flexible enough so as to conform to the movements of the patient, and such that the slits 48 exhibit the unidirectional fluid flow properties discussed above in connection with FIGS. 4 and 5.

In the preferred embodiment, cylindrical sleeve 28 is made from a polyurethane material. Also, Teflon, nylon or polyethylene materials may be suitable. The sleeve material can have a Shore A durometer in the range from about 80 to about 100 and Shore D durometer in the range of 40 to 70, and preferably will be in the range from about Shore D 40 to about 55.

It will be appreciated that the valve means may be comprised of a variety of equivalent structures. For instance, valve means could be comprised of a plurality of holes formed through the cylindrical wall 36 of the cylindrical sleeve 28. Further, this structure could provide a one way fluid flow function if the holes are made sufficiently large with respect to the width of interior lumen 38. In such an embodiment, the pressures exerted by bodily fluids, such as interstitial blood pressure, would compress the interior lumen 38 and thereby prevent back-flow of bodily fluids back into the interior lumen 38 through the holes. An illustrative example of such an embodiment is described in further detail below in connection with FIGS. 17A through 18B.

With continued reference to FIGS. 1 and 2, formed on the hub 40 near proximal end 32 of the cylindrical sleeve 28 is a suture attachment ring 47. Once the cylindrical sleeve 28, in conjunction with the insertion sheath cannula 14, has been positioned within the portion of subcutaneous tissue 20, the physician can suture, or otherwise attach, the cylindrical sleeve 28 to the patient via the suture attachment ring 47. In this manner, the cylindrical sleeve 28 will stay correctly positioned within the portion of subcutaneous tissue 20 during subsequent medical procedures, such as a PTCA.

This insures that medical personnel can administer a fluid medicament, such as an anesthetic agent, to the subcutaneous tissue 20 without first having to reposition the cylindrical sleeve 28.

Figure 6:
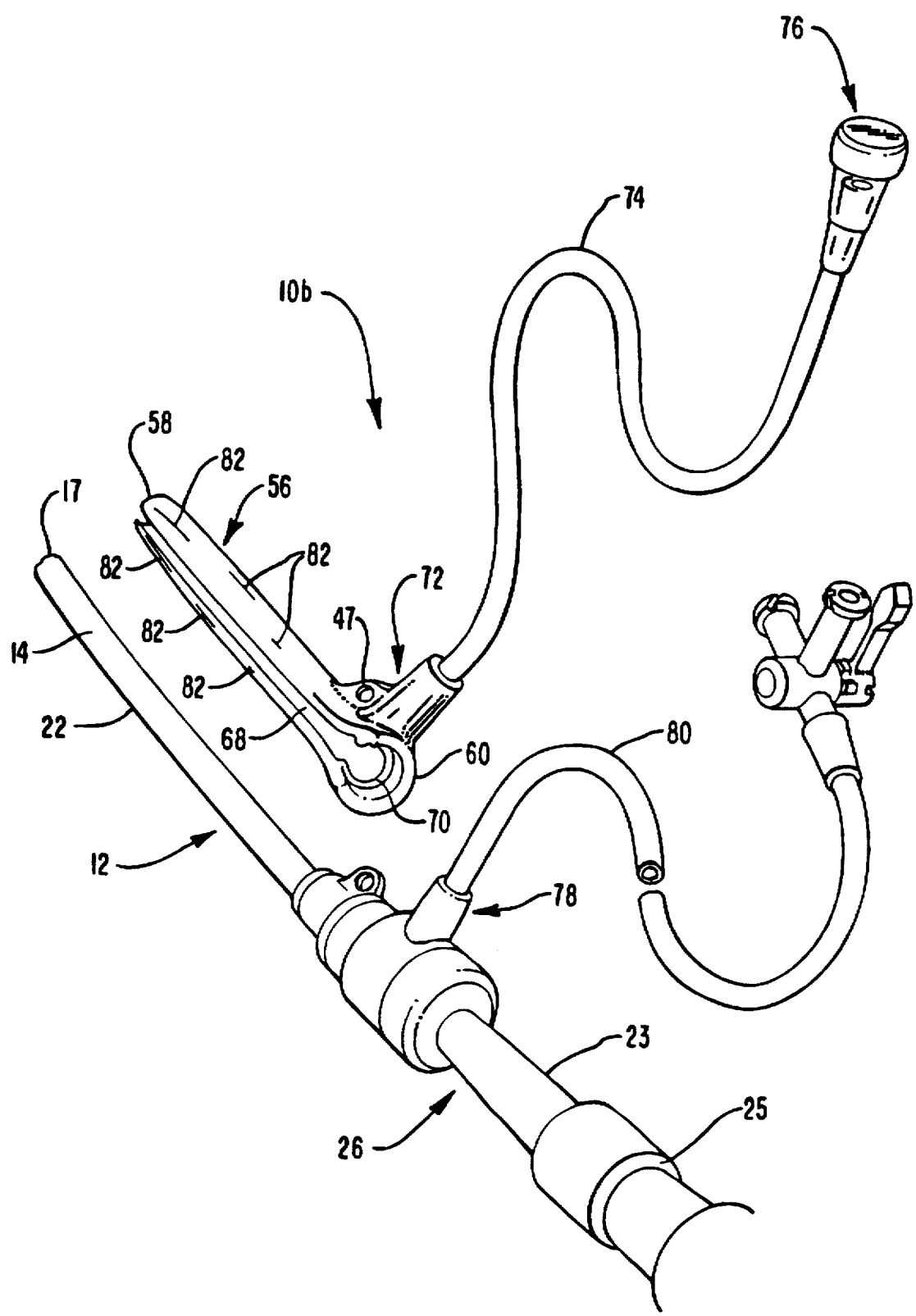
FIG. 6 is an exploded perspective view of another presently preferred embodiment of the catheter apparatus of the present invention.
Figure 7:
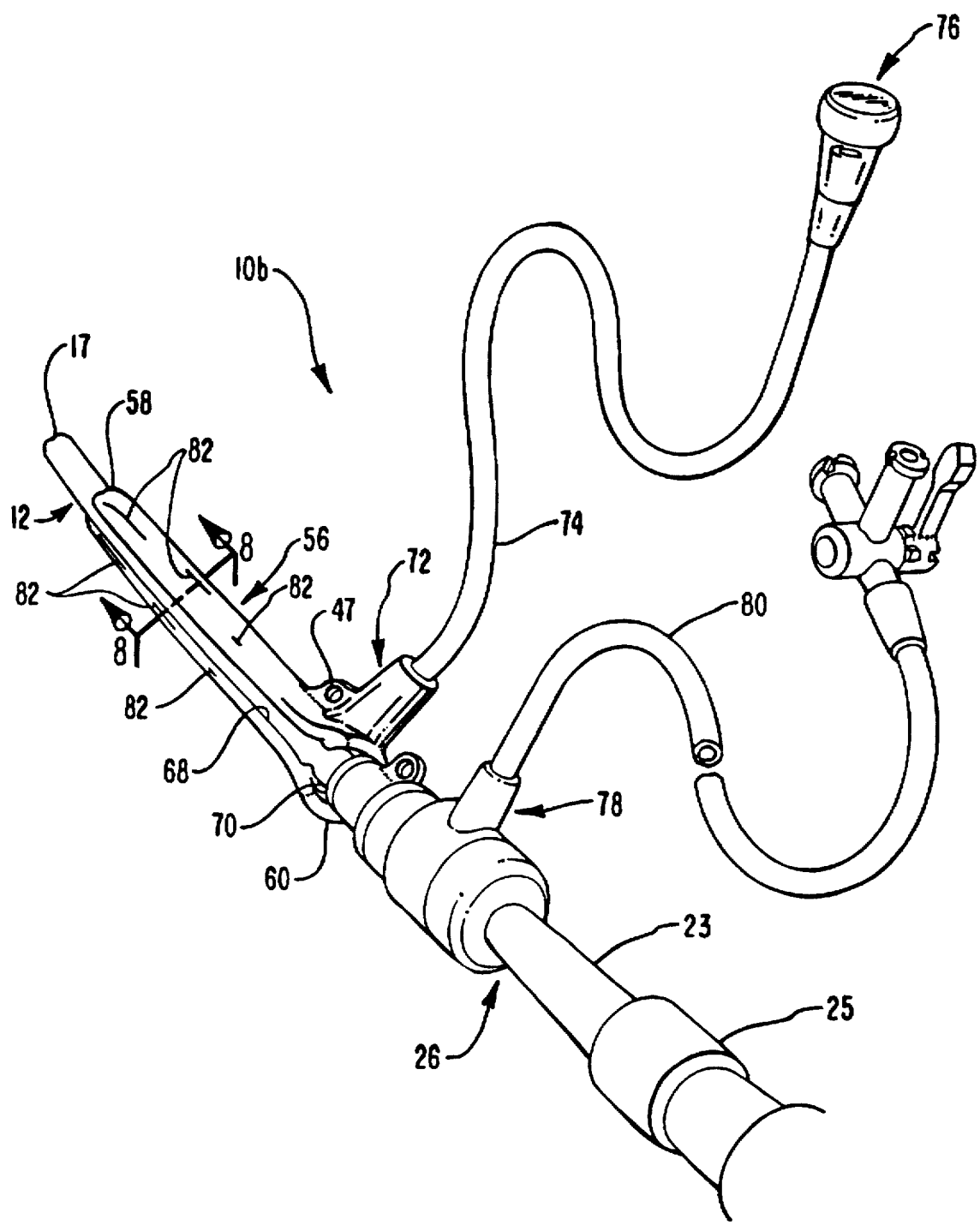
FIG. 7 is a perspective view of the anesthetizing sheath of FIG. 6 mounted to a catheter device.
Figure 8:
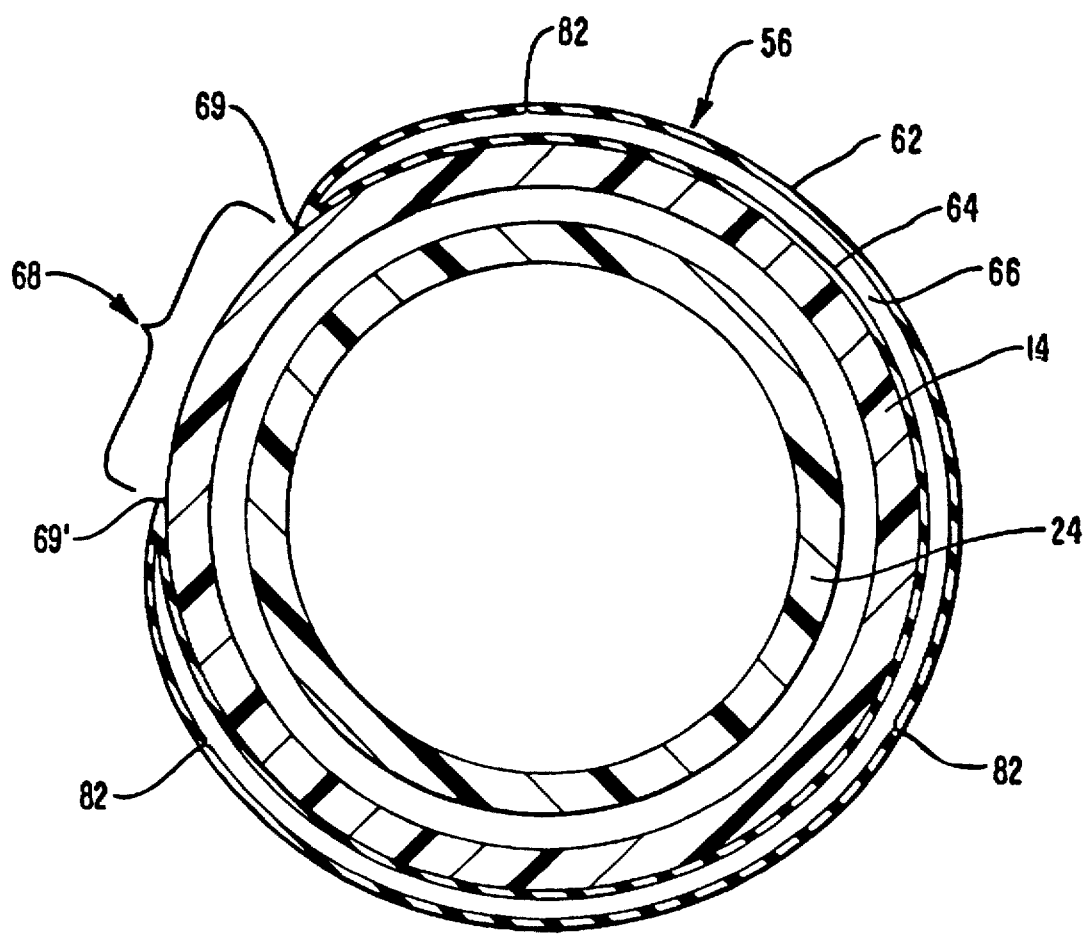
FIG. 8 is a cross-sectional view taken along line 8—8 in FIG. 7.

Another embodiment of the catheter apparatus of the present invention is illustrated in FIGS. 6 through 8, and is designated generally at 10b. Catheter apparatus 10b includes a catheter means, as for example a catheter device designated generally at 12 which is essentially the same as the catheter device discussed in conjunction with FIGS. 1 through 3. That discussion will not be repeated here.

The indwelling catheter apparatus 10b also comprises a a sheath means, as for example a hollow cylindrical sleeve 56, for placement onto at least a portion of the cannula 14 at a point intermediate of the distal end 17 and the proximal hub end 26 of the cannula 14. However, unlike the embodiment shown in FIGS. 1 through 3, the sheath means of FIGS. 6 through 8 can be selectively attached and detached to the cannula 22, as discussed in further detail below.

As is shown in FIGS. 6 and 7, cylindrical sleeve 56 has a distal end 58 and a proximal end 60. Hollow cylindrical sleeve 56 further has an inner diameter which is greater than the outer diameter of cannula 14. This relationship is also shown in the cross-sectional view of FIG. 8. Also shown in FIG. 8 is how cylindrical sleeve 56 is positioned, in a tight fitting manner, on cannula 14 so as to be concentric with the cannula 14. Preferably, distal end 58 of cylindrical sleeve 56 is tapered with respect to the outer surface 22 of cannula 14, so that the cylindrical sleeve 56 can be inserted with little or no trauma through the portion of subcutaneous tissue 20 when it is mounted to the cannula 14.

The cylindrical sleeve 56 further comprises a means for delivering fluid medicament, such as an anesthetic agent, to the subcutaneous tissue 20 surrounding the sleeve 56. The fluid medicament delivering means comprises, for example, a means for defining an interior lumen running from the distal end 58 to the proximal end 60 of the sleeve 56, a hub means through which the fluid medicament is delivered to the interior lumen, and a plurality of one way valve means for communicating the fluid medicament from the interior lumen to the subcutaneous tissue 20 surrounding the sleeve 56 and for preventing fluids from entering the interior lumen.

By way of example, and referring now to FIG. 8, cylindrical sleeve 56 is illustrated as being comprised of a cylindrical outer wall 62 that is formed over a concentric cylindrical inner wall 64 in a spaced apart relationship. Thus, in this embodiment, an interior lumen 66 is provided by the space between the outer wall 62 and the inner wall 64.

By way of further example and with continued reference to FIGS. 6 and 7 in combination, the hub means is comprised of a first hub 72. In the preferred embodiment, first hub 72 is joined in a fluid tight manner to the proximal end 60 of the cylindrical sleeve 56. First hub 72 further comprises, for example, a first passageway means, such as a first hub lumen (not shown), for communicating the anesthetic agent to the interior lumen 66. As is shown in FIG. 6 and 7, the first hub 72 can be attached, for example, to an external tube 74 through which the anesthetic agent can be introduced to the internal lumen 66, as for example by a syringe (not shown), via an infusion port 76.

FIGS. 6 through 8 further illustrate the preferred embodiment of the plurality of one way valve means spaced along the cylindrical sleeve 56. As is shown, each valve means is comprised of a one way slit 82 that is formed through outer wall 62 of cylindrical sleeve 56. These slits 82 are preferably substantially identical to the one way slits 48 described above in connection with FIGS. 1 through 3, and that discussion will not be repeated here.

As is further shown in FIGS. 6 through 8, in this particular embodiment sleeve 56 is further comprised of a means for selectively attaching and detaching the sleeve 56 from the cannula 14. For example, the means for selectively attaching and detaching is illustrated as being comprised of a continuous slit 68 that extends longitudinally along the entire length of the cylindrical sleeve 56. Slit 68 has a width such that the cylindrical sleeve 56 can be detachably mounted to the cannula 14 through the slit 68. The cylindrical sleeve 56 in such a mounted position is illustrated in FIGS. 7 and 8.

Referring now to FIG. 8, when cylindrical sleeve 56 is mounted to cannula 14, the cylindrical inner wall 64 is in continuous contact with the outer surface of cannula 14. This tight fitting position is maintained by the resilient properties that are preferably exhibited by cylindrical sleeve 56. As is further shown, the edges 69 and 69' where the outer wall 62 meets inner wall 64 are tapered with respect to the outer surface of the cannula 14. This permits the cylindrical sleeve 56 to be inserted with less trauma into the subcutaneous tissue, and it further forms a tight seal between the cylindrical sleeve 56 and cannula 14 so as to prevent bodily fluids from leaking between sleeve 56 and cannula 14. The sheath means of this embodiment is also comprised of a means for sealing the sheath means in a fluid tight manner around the cannula 14 so as to prevent fluids, such as blood from the body, from escaping between the cannula 14 and the sleeve 56. For example, as is shown in both FIGS. 6 and 7, this sealing is accomplished by placing an O-ring 70 between the cylindrical sleeve 56 and the outer surface of the cannula 14. Thus, when the cylindrical sleeve 56 is mounted to the cannula 14, O-ring 70 forms a fluid-tight seal, and thereby prevents any bodily fluids from leaking between sleeve 56 and cannula 14. Cylindrical sleeve 56 also has formed thereon a suture attachment ring 47, similar to the ring 47 discussed above in connection with FIGS. 1 through 3.

In the embodiment of FIGS. 6 and 7, the indwelling catheter apparatus further includes a second hub means, as for example hub 78, for providing fluid communication to the cannula 14. Hub 78 is joined in a fluid tight manner to the proximal end of cannula 14. As is also shown, hub 78 can be connected to external tube 80, through which fluids may be infused to cannula 14. A dilation catheter may be introduced into cannula 14 through tubing 23 and connector 25.

Figure 9:
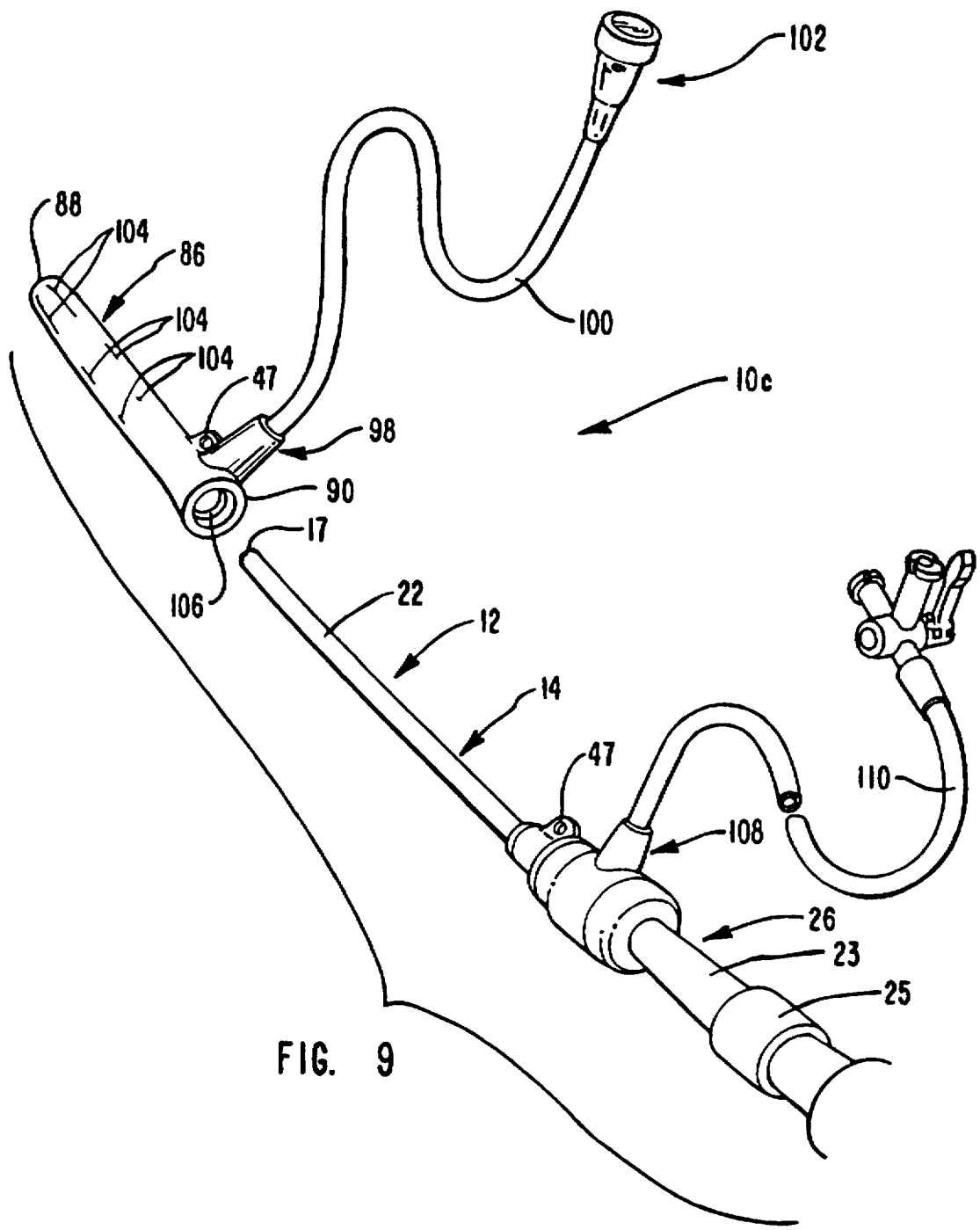
FIG. 9 is an exploded perspective view of another presently preferred embodiment of the catheter apparatus.
Figure 10:
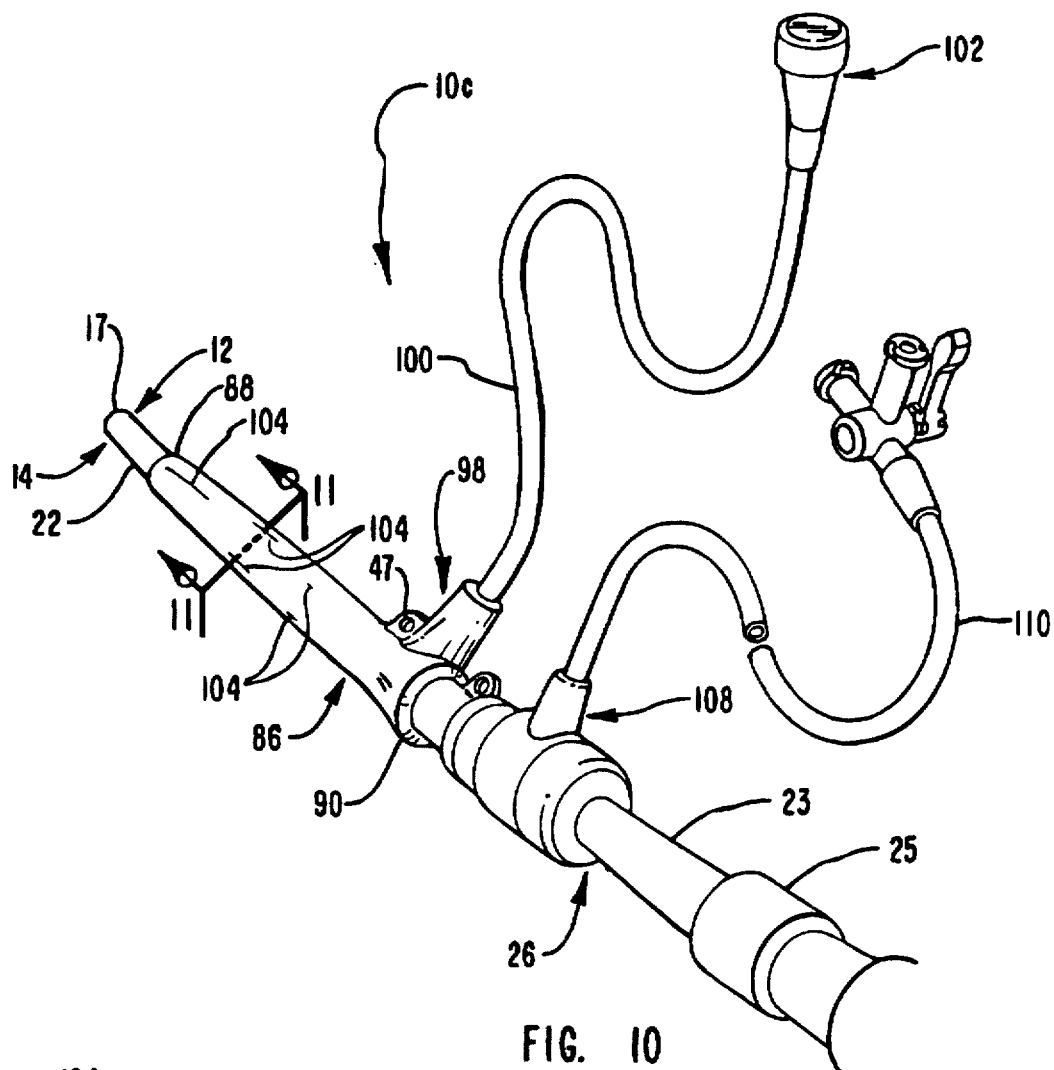
FIG. 10 is a perspective view of the anesthetizing sheath of FIG. 9 mounted to a catheter device.
Figure 11:
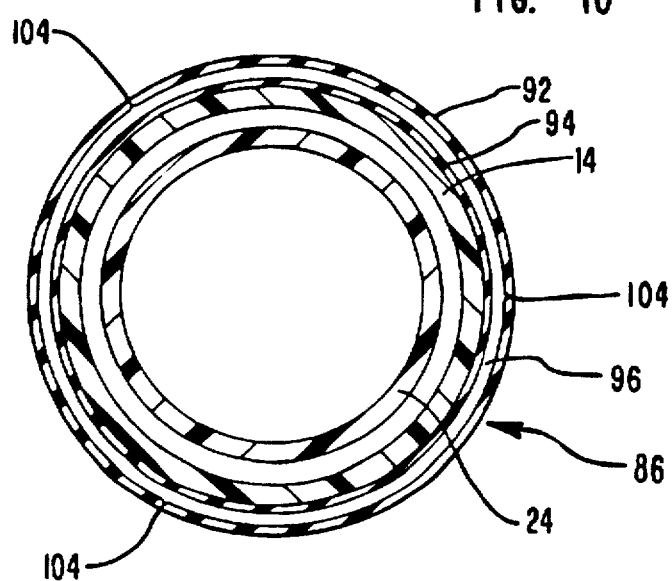
FIG. 11 is a cross-sectional view taken along line 11—11 of FIG. 10.

Yet another embodiment of the indwelling catheter apparatus of present invention is illustrated in FIGS. 9 through 11, and is designated generally at 10c. Indwelling catheter apparatus 10c also includes a catheter means, as for example a catheter device, which is essentially the same as the catheter device discussed in conjunction with FIGS. 1 through 3.

The indwelling catheter apparatus 10c also comprises a sheath means, as for example a hollow cylindrical sleeve 86, for placement onto at least a portion of the cannula 14 at a point intermediate of the distal end 17 and the proximal hub end 26 of the cannula 14. As with the embodiment shown in FIGS. 6 through 8, the sheath means of FIGS. 9 through 11 can be selectively attached and detached to the cannula 14, as will be discussed in further detail below.

As is shown in FIGS. 9 and 10, cylindrical sleeve 86 has a distal 88 and a proximal end 90. Hollow cylindrical sleeve 86 further has an inner diameter which is greater than the outer diameter of cannula 14. This relationship is also shown in the cross-sectional view of FIG. 11. Also shown in FIG.

11 is cylindrical sleeve 86 positioned in a tight fitting manner on cannula 14 so as to be concentric with the cannula 14. Preferably, distal end 88 of cylindrical sleeve 86 is tapered with respect to the outer surface of cannula 14, so that the cylindrical sleeve 86 can be inserted with little or no trauma through the portion of subcutaneous tissue 20 when it is mounted to the cannula 14.

The cylindrical sleeve 86 further comprises a means for delivering fluid medicament, such as an anesthetic agent (not shown), to the subcutaneous tissue 20 surrounding the sleeve 86. The fluid medicament delivering means comprises, for example, a means for defining an interior lumen running from the distal end 88 to the proximal end 90 of the sleeve 86, a hub means through which the fluid medicament is delivered to the interior lumen, and a plurality of one way valve means for communicating the fluid medicament from the interior lumen to the subcutaneous tissue surrounding the sheath means and for preventing fluids from entering the interior lumen.

By way of example, and referring now to FIG. 11, cylindrical sleeve 86 is illustrated as being comprised of a cylindrical outer wall 92 that is formed over a concentric cylindrical inner wall 94 in a spaced apart relationship. Thus, in this embodiment, interior lumen 96 is provided by the space which is formed between the outer wall 92 and the inner wall 94.

By way of further example and with reference now to FIGS. 9 and 10 in combination, the hub means is comprised of a first hub 98 joined in a fluid tight manner to the proximal end 90 of the cylindrical sleeve 86. First hub 98 further comprises, for example, a first passageway means, such as a first hub lumen (not shown), for communicating the fluid medicament to the interior lumen 96. As is shown in FIGS. 9 and 10, the first hub 98 can be attached, for example, to an external tube 100 through which the fluid medicament can be introduced to the internal lumen 96, as for example by syringe (not shown), via an infusion port 102.

FIGS. 9 through 11 further illustrate the preferred embodiment of the plurality of one way valve means spaced along the cylindrical sleeve 86. As is shown, each valve means is comprised of a one way slit 104 that is formed through outer wall 92 of cylindrical sleeve 86. These slits 104 are preferably substantially identical to the one way slits 48 described above in connection with FIGS. 1 through 3.

As is further shown in FIGS. 9 and 10, in this particular embodiment the sleeve 86 is further comprised of a means for selectively attaching and detaching the cylindrical sleeve 86 from the cannula 14. For example, selective attachment and detachment is illustrated as being accomplished by longitudinally sliding the hollow cylindrical sleeve 86 onto cannula 14. The cylindrical sleeve 86 in such a mounted position is illustrated in FIGS. 10 and 11.

When cylindrical sleeve 86 is thus mounted to cannula 14, the cylindrical inner wall 94 is in a continuous and tight fitting contact with the outer surface of cannula 14. The inner diameter of the cylindrical sleeve 86 with respect to the outer diameter of cannula 14 is such that the sleeve 86 remains positioned on the cannula 14 in a slidable, yet tight fitting manner.

The sleeve 86 of this embodiment is also comprised of a means for sealing the sleeve 86 in a fluid tight manner around the cannula 14 so as to prevent fluids, such as blood from the body, from escaping between the cannula 14 and the sleeve 86. For example, as is shown in FIG. 9, this sealing means is accomplished by placing an O-ring 106 between the inner surface of the cylindrical sleeve 86 and the outer surface of the cannula 14. Thus, when the cylindrical sleeve 86 is mounted to the cannula 14, O-ring 106 forms a fluid-tight seal, and thereby prevents any bodily fluids from leaking between sleeve 86 and cannula 14. Cylindrical sleeve 86 also has formed thereon a suture attachment ring 47, similar to the ring 47 discussed above in connection with FIGS. 1 through 3.

In the embodiment of FIGS. 9 and 10, the indwelling catheter apparatus further includes a second hub means, as for example hub 108, for providing fluid communication to the cannula 14. Hub 108 is joined in a fluid tight manner to proximal hub end 26 of cannula 14. As is also shown, hub 108 can be connected to external tube 110, through which fluids may be infused to cannula 14.

As discussed, the cylindrical sleeves 56, 86 of the two embodiments of FIGS. 6 through 8 and 9 through 11 are not permanently mounted to any particular catheter device 12, but can be selectively attached and detached to preexisting catheter devices. Consequently, the versatility of a single cylindrical sleeve is greatly enhanced because it can be used with any one of a variety of catheter devices that are already on hand. Thus, when using a preexisting catheter device, medical personnel can retrofit the device with a cylindrical sleeve discussed in connection with FIGS. 6 through 11, and provide the patient with the pain relief that would not otherwise be available with that catheter device. Importantly, this retrofit capability provides the advantages of pain relief, yet simultaneously protects any investment already made in a stock of preexisting catheter devices.

It will be appreciated that although the only difference between the embodiment of FIGS. 6 through 8 and the embodiment of FIGS. 9 through 11 lies in how the cylindrical sleeve 56 or 86 is attached and detached to the cannula 14, the difference in how the two embodiments are used is more significant. In use, cylindrical sleeve 56 (FIGS. 6–8) attaches and detaches to the cannula 14 by way of the longitudinal slit 68 formed along the length of the sleeve 56. Thus, the sleeve 56 can be attached to a cannula 14 even if the cannula 14 has already been inserted in the patient. For instance, a doctor may insert a catheter device, such as an insertion sheath, perform the underlying procedure and, when completed, snap on the cylindrical sleeve 56 to the proximate portion of the cannula 14. Since the patient is still locally anesthetized from the previously performed medical procedure, the sleeve 56 can then be inserted into the portion of subcutaneous tissue 20 with the cannula 14. When the cannula 14 is later retracted (and the previously administered local anesthetic has worn off) the doctor can readminister a local anesthetic to the subcutaneous tissue 20 through sleeve 56 and then painlessly retract the cannula 14. In this way, the doctor or medical technician is not distracted by the extra equipment, tubes, infusion ports, etc. associated with cylindrical sleeve 56 while the underlying medical procedure, such as a PTCA, is being done.

In contrast, cylindrical sleeve 86 (FIGS. 9–11) attaches and detaches to the cannula 14 by sliding the sleeve 86 onto the cannula 14. Consequently, the sleeve 86 of this embodiment cannot be placed on a cannula 14 that has already been inserted in a patient, and must necessarily be positioned on the cannula 14 before the underlying medical procedure is done and thus before cannula 14 is initially inserted into the patient. However, under certain circumstances this approach may be entirely acceptable and/or desirable.

Figure 12:
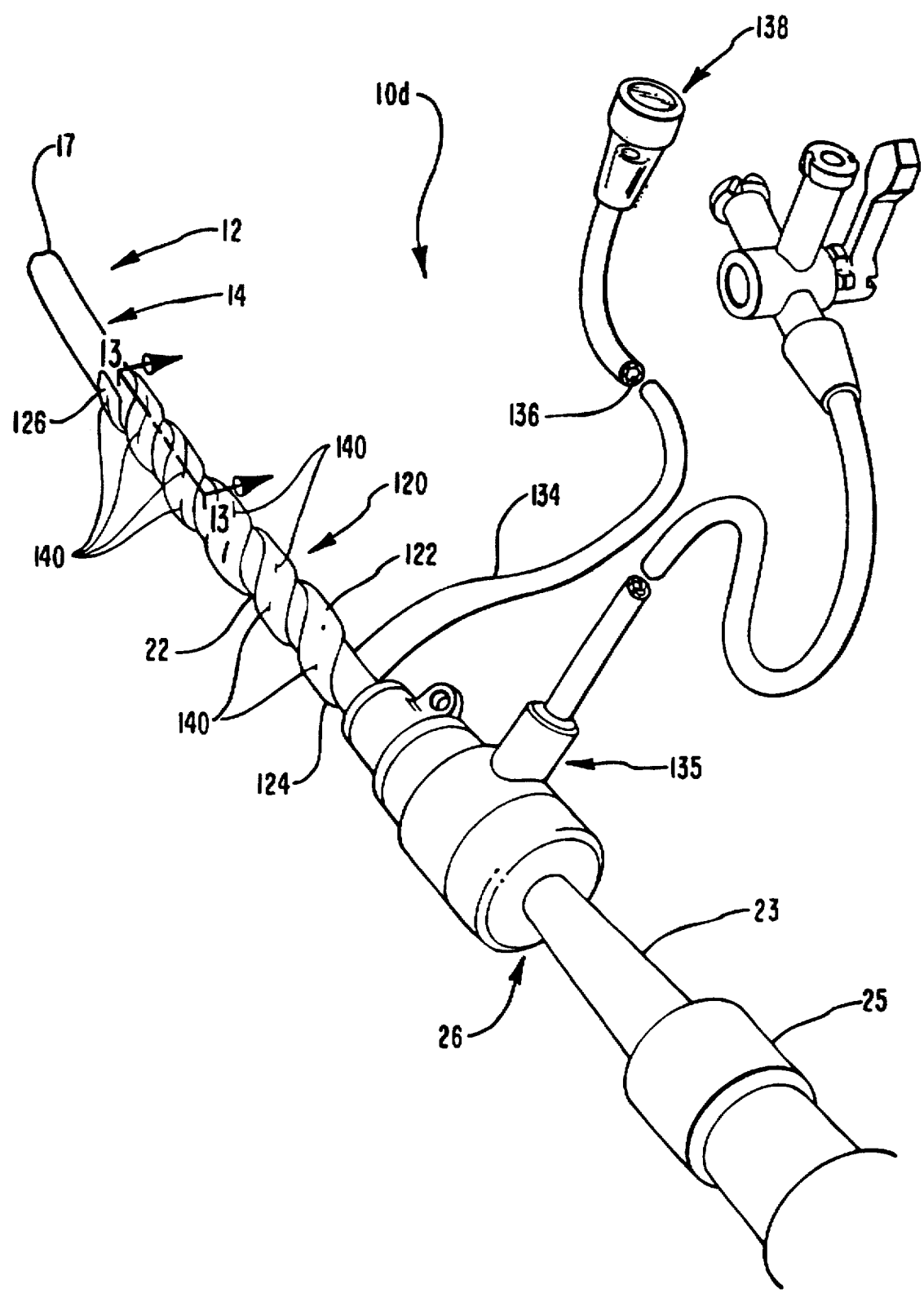
FIG. 12 is a perspective view of still another embodiment of the present invention.
Figure 13:
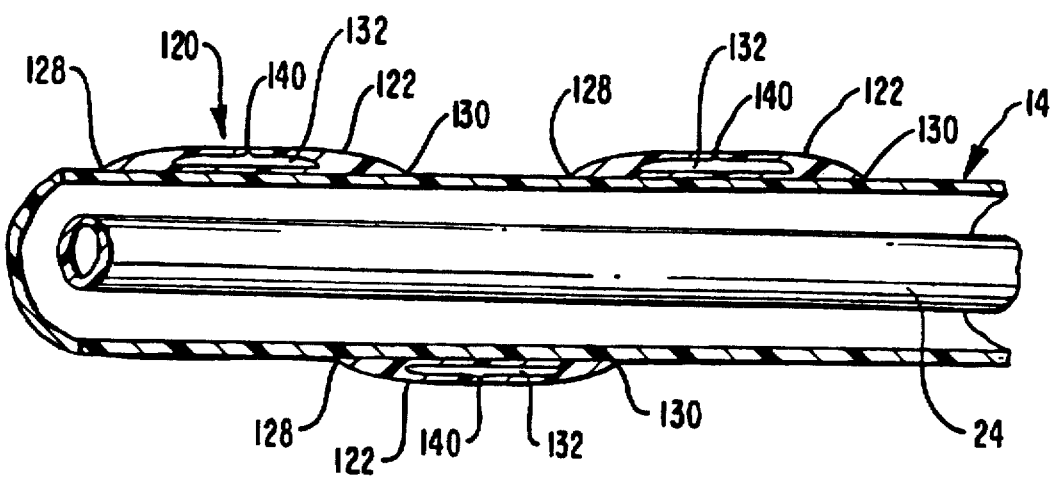
FIG. 13 is an enlarged cross-sectional view taken along lines 13—13 of FIG. 12.

FIGS. 12 and 13 illustrate yet another embodiment of the indwelling catheter apparatus of the present invention, designated generally at 10d. As in the embodiments previously discussed, catheter apparatus 10d includes a catheter means, as for example a catheter device, which is essentially the same as the catheter device of the previous embodiments.

The indwelling catheter apparatus 10d also has a sheath means for placement onto the cannula 14. By way of example and referring now to FIG. 12, sheath means is comprised of a helical sheath, designated generally at 120. As is shown, helical sheath 120 is comprised of a single band 122 that is wound in a helical fashion so as to conform to the cylindrical outer periphery of the cannula 14. The helical sheath 120 has a proximate end 124 and a distal end 126, and is preferably positioned on the cannula 14 so that it can be disposed within the area of subcutaneous tissue 20 in conjunction with the cannula 14 (in the same manner illustrated in FIG. 2).

Referring now to FIG. 13, the band 122 that forms helical sheath 120 has a substantially flat cross-section when it is placed on the cannula 14. Further, when positioned on the cannula 14, band 122 has successive leading edges 128 and trailing edges 130 that are tapered with respect to the outer surface of the cannula 14. Advantageously, when the helical sheath 120 is mounted to the cannula 14, this flat cross-section and the tapered leading and trailing edges 128, 130 of band 122 act so as to ease the insertion and retraction of the helical sheath 120 through the patient's skin and subcutaneous tissue 20 when it is mounted to the cannula 14. Similarly, this configuration minimizes trauma to the skin or subcutaneous tissue 20 when the helical sheath 120 is inserted and retracted.

Figure 13A:
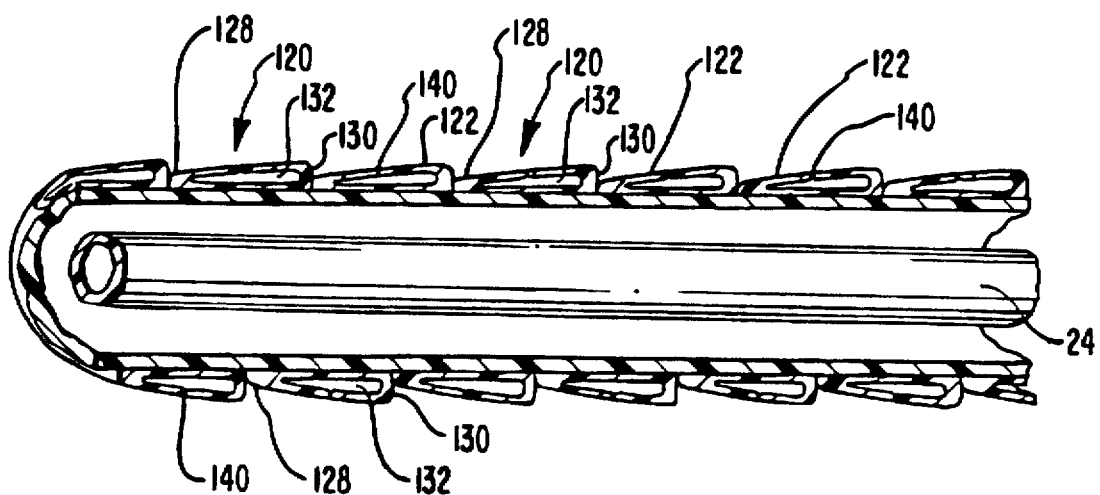
FIG. 13A is an enlarged cross-sectional view showing an alternative embodiment of the catheter apparatus of FIG. 12.

Alternatively, FIG. 13A illustrates another cross-sectional shape that may be formed by band 122. In this embodiment, band 122 is placed on cannula 14 in a tight helical fashion such that the leading edges 128 abut against the adjacent trailing edges 130. Further, each leading edge 128 slopes upwardly towards the trailing edge 130 to form an overall tapered shape. In this way, the helical sheath 120 has an overall tapered shape so as to permit easier insertion through the patient's skin and subcutaneous tissue 20.

Helical sheath 120 is further comprised of a fluid delivery means for delivering a fluid medicament, such as an anesthetic agent, to the subcutaneous tissue 20 in which the helical sheath 120 is disposed. By way of example, FIGS. 12 and 13 illustrate how the fluid delivery means is preferably comprised of a means for defining an interior lumen running from the distal end 126 to the proximal end 124 of helical sheath 120. As is shown, lumen means is comprised of an interior lumen 132 that is defined by a hollow portion formed within band 122. The hollow portion that defines interior lumen 132 extends along the entire length of helical sheath 120.

Helical sheath 120 is also preferably comprised of a hub means through which the anesthetic agent is delivered to the interior lumen 132. As FIG. 12 illustrates, hub means is comprised, for example, of a tube 134 which is coupled in a fluid tight manner to the proximal end 124 of the helical sheath 120. Tube 134 has a single lumen 136 that is in fluid communication with the interior lumen 132. Anesthetic agent can be delivered to interior lumen 132 through a fluid injection port 138 connected to the opposite end of tube 134. FIG. 12 further illustrates how hub means also comprises, for example, a hub 135 that is connected in a fluid tight manner to the proximal hub end 26 of cannula 14. Hub 135 is essentially identical to hub 108 discussed in connection with the embodiment of FIG. 10, and thus that discussion will not be repeated.

With continued reference to FIG. 12, helical sheath 120 also comprises a plurality of one way valve means for communicating the anesthetic agent from the interior lumen 132 to the subcutaneous tissue 20 surrounding the sheath 120, and at the same time, for preventing bodily fluids, such as blood, from entering the interior lumen 132. For example, FIGS. 12 and 13 illustrate how the valve means are each comprised of a one way slit 140 that is formed through the band 122 to interior lumen 132. One way slits 140 are placed uniformly along helical sheath 120, and are essentially identical to the one way slits discussed above in connection with the embodiments of FIGS. 1 through 11.

As discussed generally, helical sheath 120 may further comprise a means for selectively attaching and detaching the helical sheath 120 to the cannula 22. This function is provided by wrapping the helical sheath 120 onto the longitudinal length of cannula 14 so that the helical sheath 120 is concentrically positioned on the cannula, as is illustrated in FIG. 12. It will be appreciated that, like the embodiment of FIGS. 6 through 8, helical sheath 120 can be detachably mounted to a cannula 14 even after the cannula 14 has already been inserted into the patient. Preferably, the helical sheath 120 exhibits sufficient resilient properties such that once it is positioned on the cannula 14, it remains positioned in a tight fitting manner. Alternatively, once helical sheath 120 has been detachably mounted to the cannula 14, the medical technician may further adhere the sheath 120 to the cannula 14 by applying a small amount of liquid adhesive. Thus, helical sheath 120 can be selectively used on a variety of preexisting catheter devices. Alternatively, cannula 14 can be manufactured with a helical sheath 120 premounted in the manner illustrated in FIG. 12. In this instance, helical sheath 120 would be affixed permanently to the catheter device 12 by fusing, or similarly adhering it to the cannula 14.

Figure 14:
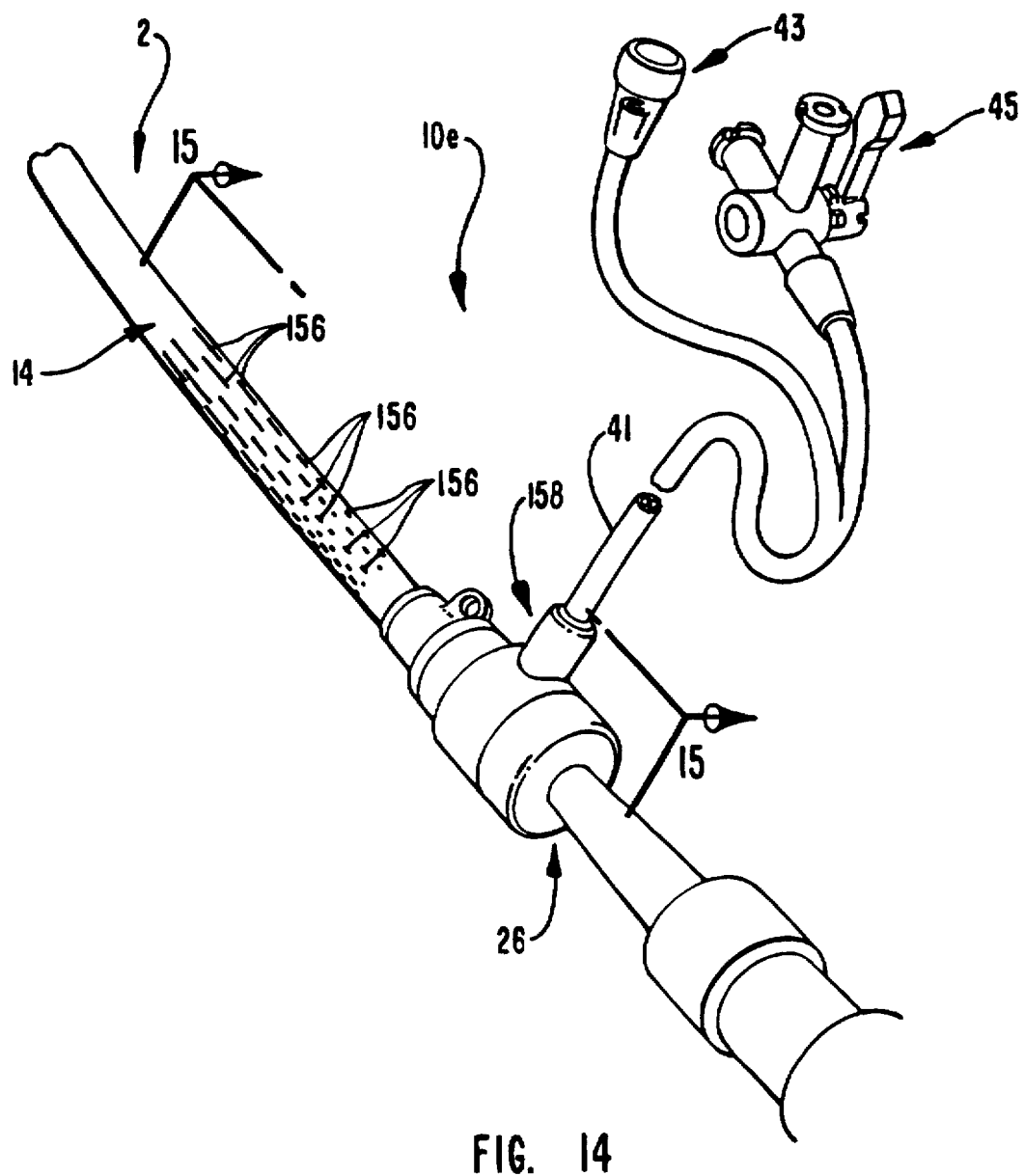
FIG. 14 is a perspective view of yet another embodiment of a catheter apparatus constructed in accordance with the inventive concepts of the present invention.
Figure 15:
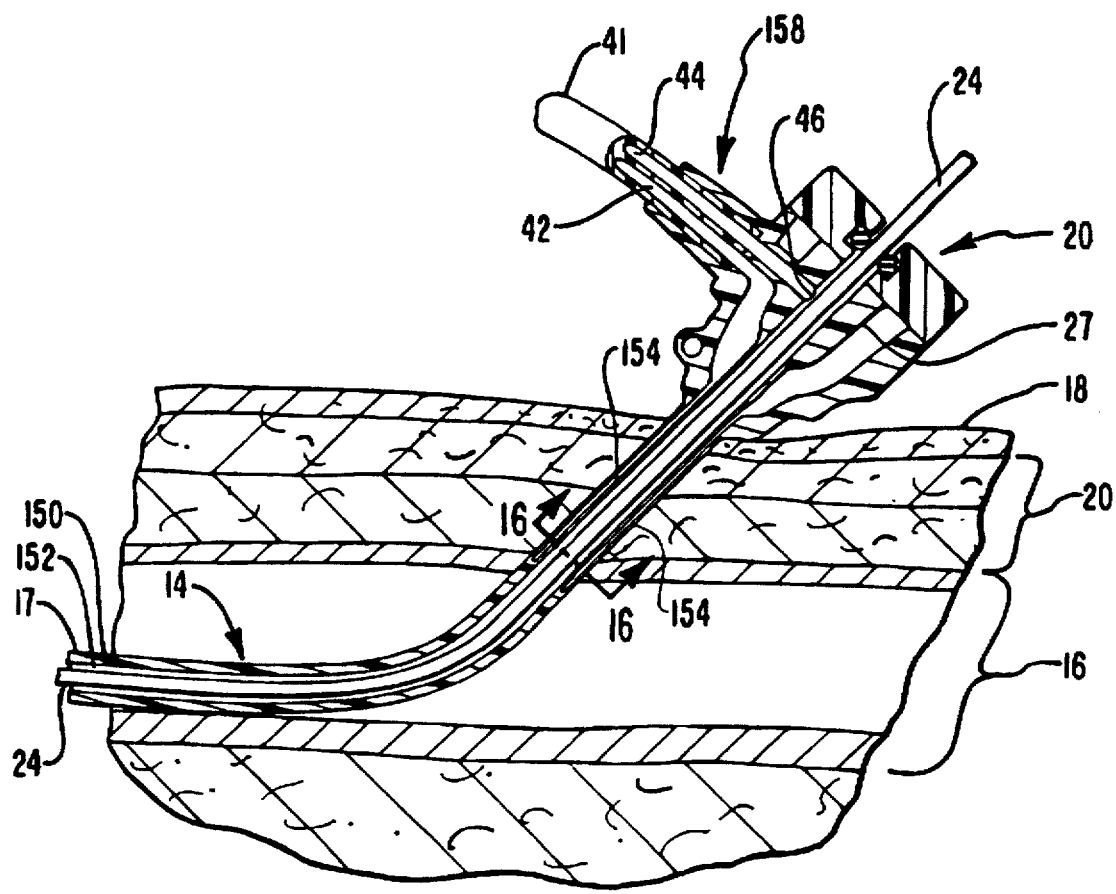
FIG. 15 is a cross-sectional view taken along lines 15—15 of FIG. 14, and further illustrates the catheter apparatus of FIG. 14 disposed within a portion of a patient's body.
Figure 16:
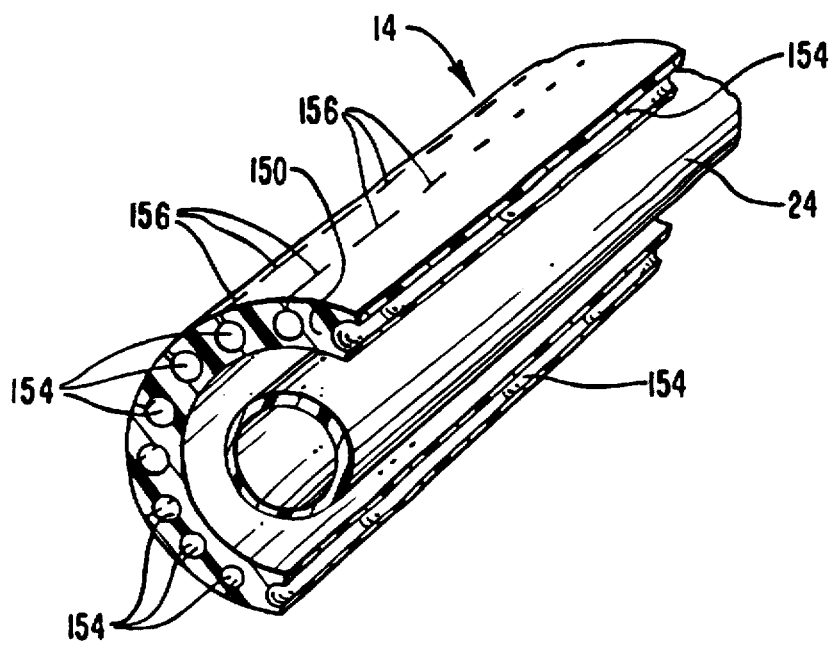
FIG. 16 is an enlarged cross-sectional view taken along lines 16—16 of FIG. 15.

Referring now to FIGS. 14 through 16, yet another preferred embodiment of indwelling catheter apparatus, designated generally at 10e, is shown. Indwelling catheter apparatus 10e includes a catheter means, as for example a catheter device 12, that has a cannula 14 for insertion through subcutaneous tissue 20 into a patient's body (shown in FIG. 15). The catheter device 12 is essentially identical to the catheter device described in conjunction with the previous embodiments, having an indwelling distal end 17 and a proximal hub end 26. FIG. 15 further illustrates how cannula 14 is a cylindrical tube having a cylindrical outer wall 150, through which a primary lumen 152 runs.

Indwelling catheter apparatus 10e also comprises a means for delivering a fluid medicament, such as an anesthetic agent, to essentially only the area of subcutaneous tissue 20 through which the cannula 14 is inserted. For example, in the embodiment of FIGS. 14 through 16, the means for delivering a anesthetic agent is comprised of a secondary lumen that is formed in the outer wall 150 of the cannula 14. FIGS. 15 and 16 illustrate how the secondary lumen is preferably comprised of a plurality of longitudinal bores 154 formed within the outer wall 150. As is further shown, the plurality of bores 154 are uniformly spaced about the circumference of the cannula 14, and each bore 154 is substantially parallel to the primary lumen 152 running through the cannula 14. Further, the plurality of bores 154 that form the secondary lumen are preferably formed in the cannula 14 outer wall 150 so that they are substantially disposed within the area of subcutaneous tissue 20 once the cannula 14 has been inserted within the patient's body. In this way, secondary lumen, as defined by the plurality of bores 154, can distribute the anesthetic agent to the subcutaneous tissue 20 evenly and uniformly.

The anesthetic agent is communicated to the surrounding subcutaneous tissue 20 from the secondary lumen 154 through a plurality of one way valve means, which also act to prevent bodily fluids from entering the secondary lumen 154. As FIG. 14 illustrates, the one way valve means are each comprised of a single one way slit 156 that is formed through the outer wall 150 to each of the plurality of longitudinal bores 154. This is illustrated in further detail in the exploded cross-section view of FIG. 16, where one way slits 156 are illustrated. Each of the one way slits 156 are substantially identical to the one way slits discussed above in connection with the other preferred embodiments.

To deliver the anesthetic agent to the secondary lumen 154, the fluid delivery means is further comprised of a hub means. This hub means is illustrated as being comprised of a single hub 158, that is joined in a fluid tight manner to the proximal hub end portion 27 of the cannula 14. FIGS. 14 and 15 illustrate how hub 158 is formed with a first hub lumen 42 and a second hub lumen 44. First hub lumen 42 is coupled to each of the longitudinal bores 154 that form the secondary lumen so as to provide a passageway for delivering anesthetic agent. Similarly, second hub lumen 44 is coupled to the primary lumen 152 via a cannula access hole 46, thereby providing a separate fluid passageway for that lumen. As FIG. 14 illustrates, the first and second hub lumens 42, 44 are connected to a multi-lumen tube 41, through which the first hub lumen 42 is connected to an infusion port 43, and second hub lumen 44 is connected to an I.V. valve assembly 45. Thus, anesthetic agent can be delivered to the bores 154 that form the secondary lumen with a syringe by using infusion port 43.

Figure 17A:
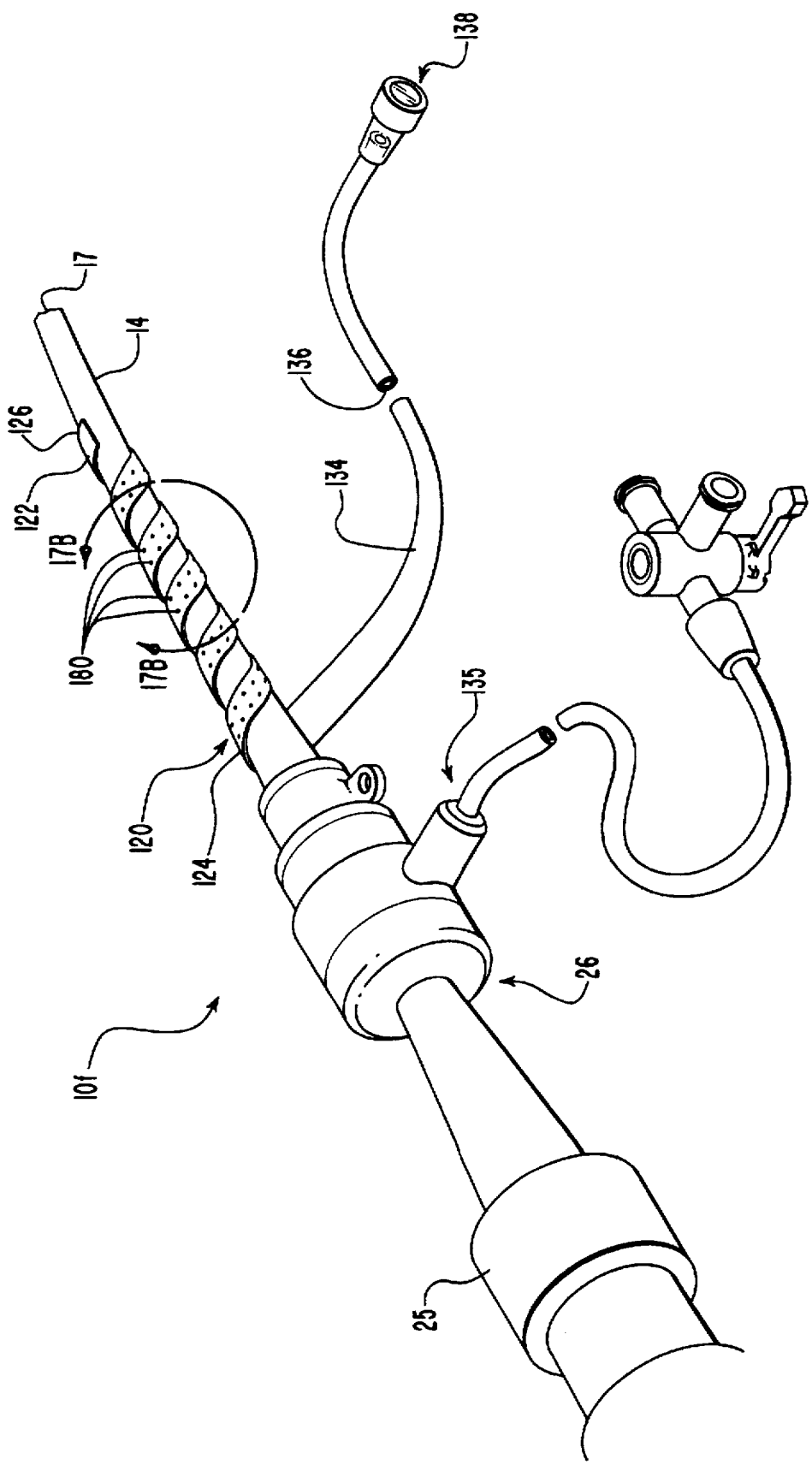
FIG. 17A is a perspective view of yet another presently preferred embodiment of the anesthetizing sheath mounted to a catheter device.

Referring next to FIGS. 17A–B and 18A–B, yet another embodiment of the present invention is shown. FIG. 17A illustrates an indwelling catheter apparatus 10f having a sheath means that is comprised of a hollow elongate band, wrapped in a helical fashion about cannula 14. This helical sheath, designated generally at 120, is substantially identical to the helical sheath 120 shown in FIG. 12. The identical portions of that device are designated with like numerals in FIG. 17A, and their description will not be repeated. However the embodiment of FIG. 17A differs from that of FIG. 12 in the manner by which the valve means is constructed.

Figure 17B:
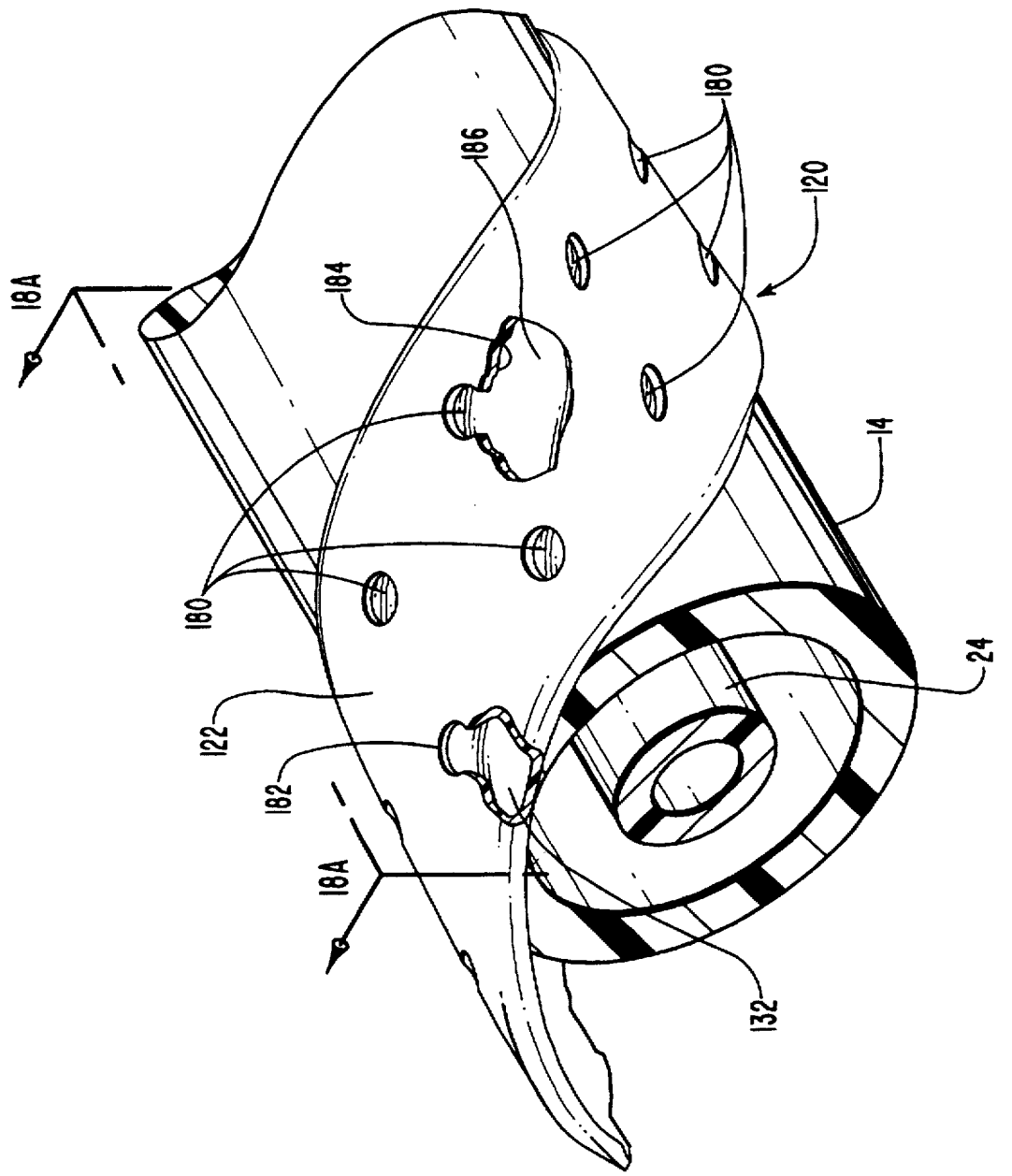
FIG. 17B is an enlarged perspective view in partial cross-section taken along lines 17B—17B of FIG. 17A.
Figure 18A:
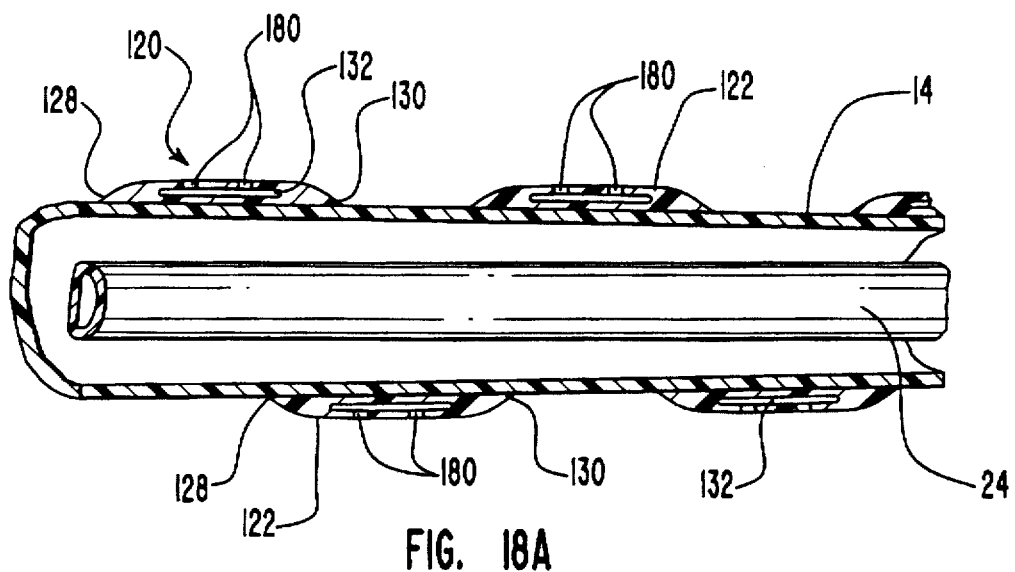
FIG. 18A is an enlarged cross-sectional view taken along lines 18A—18A of FIG. 17B.
Figure 18B:
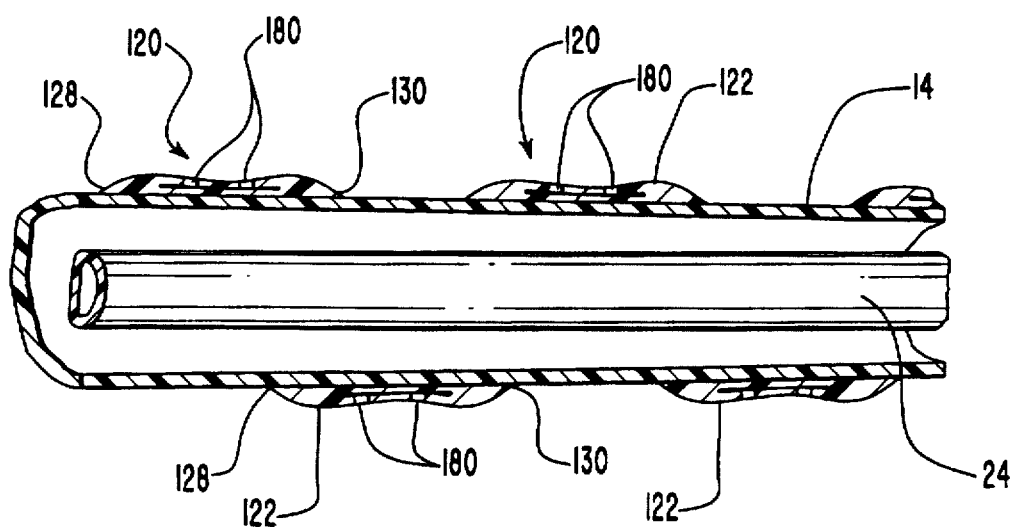
FIG. 18B is an enlarged cross-sectional view also taken along lines 18A—18A of FIG. 17B, illustrating the manner by which the interior lumen is compressed so as to close the delivery holes and thereby prevent the entry of bodily fluids into the lumen.

As is shown by way of example in FIG. 17A, in this particular embodiment the valve means is comprised of a plurality of delivery holes, designated at 180, which are substantially circular in shape and arranged uniformly along the length of the elongate band 122 that forms the helical sheath 120. FIG. 17B illustrates in further detail how each circular hole 180 is formed completely through the outer surface 182 of the band 122 so as to provide a fluid communication path with the interior lumen 132 formed within the band 122. Each hole 180 acts as a fluid path for delivering the anesthetic agent, or similar fluid medicament, to the subcutaneous tissue that is coextensive with the helical sheath 120 when it is inserted into the patient.

In the preferred embodiment, the helical sheath 120 is constructed of a slightly flexible material, such as a polyurethane, Teflon, polyethylene, or similarly flexible and medically suitable material. When fluid medicament is to be delivered to the subcutaneous tissue 20 of a patient, a positive fluid pressure is generated within the interior lumen 132, as for example by way of a syringe (not shown) that is connected to the injection port 138. In this pressurized state, illustrated in cross-section in FIG. 18A, the interior lumen 132 expands and thereby opens each of the holes 180. In this "open state," fluid medicament is delivered from the interior lumen 132, through the open delivery holes 180, and to the subcutaneous tissue 20.

The delivery holes 180 also prevent bodily fluids and/or fluid medicament from re-entering the interior lumen 132.

The flexibility of the material used to form the helical sheath 120 and the size of the holes 180 together act to perform this function. When the sheath 120 is positioned within the subcutaneous tissue 20 and medicament is not being delivered, there is no fluid pressure present within the lumen 132. Instead, the pressure exerted on the exterior surface 182 of the sheath 120, such as that which would be caused by the surrounding subcutaneous tissue 20 and the interstitial blood pressure, compresses the interior lumen 132 and causes the lumen walls 184, 186 (shown in FIG. 17B) to collapse against one another. This condition is best seen in the cross-sectional illustration of FIG. 18B. As is shown in this compressed state, the delivery holes 180 no longer provide a fluid communication path to the interior lumen 132, and external bodily fluids are thereby prevented from entering the lumen 132.

In the preferred embodiment, each of the delivery holes 180 are generally circular in shape, and are all of the same approximate diameter. However, it will be appreciated that the holes 180 can have various different shapes and yet provide the function described above. Also, if desired the hole 180 sizes can be varied, thereby controlling the amount of medicament that is delivered to the subcutaneous tissue 20.

Also, although this embodiment discloses the use of delivery holes 180 on a helical sheath 120, it will be appreciated that the holes 180 could also be used in conjunction with the other sheath embodiments described above. Referring now to FIGS. 19 and 20, another presently preferred embodiment of the invention is illustrated. FIG. 19 represents a perspective view of a catheter apparatus of the present invention, for providing fluids into a patient's central venous system, designated generally at 10g. Catheter apparatus 10g includes an indwelling cannula 200 which is preferably adapted for insertion through the chest wall and approximately within a patient's superior vena cava. A distal portion of cannula 200 is typically inserted into the jugular or subclavian vein, and a relatively proximal portion is inserted through the chest wall (typically through an existing stoma). Indwelling distal end 202 is adapted for placement within or at least approximately within the superior vena cava, while proximal hub end 206 extends outside the body. Once the cannula 200 is properly positioned, a portion 204 of the cannula 10g remains surrounded by subcutaneous tissue within the chest wall.

While reference is made to the superior vena cava and the chest wall, catheter apparatus 10g may also be successfully employed in other areas of the body in which (i) distal end 202 is in fluid communication with the circulatory system, such as by being disposed in a vein, and (ii) a portion of catheter 10g is surrounded by subcutaneous tissue.

Proper placement of catheter apparatus 10g is ensured through the use of orienting means for orienting a portion 204 of catheter apparatus 10g within the subcutaneous tissue. In at least one embodiment, the placement of catheter apparatus 10g preferably occurs in a fluoroscopic controlled setting. Thus, distal radiopaque marker 208 and proximal radiopaque marker 220 located on exterior surface 209 of cannula 200, which are examples of distal orienting means, and proximal orienting means, respectively, assist the practitioner in orienting the portion 204 of cannula 200 within the subcutaneous tissue portion of the chest wall.

Figure 21:
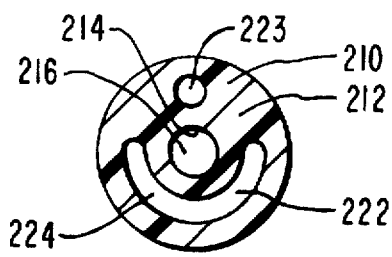
FIG. 21 is a cross-sectional view of the catheter apparatus of FIG. 19.

Once in place, catheter apparatus 10g is employed for delivering fluid into the central venous system through the use of a primary lumen 216. As shown in FIG. 20, in one embodiment, cannula 200 is comprised of a cylindrical tube 210. As shown in FIG. 21, cylindrical tube 210 has a cylindrical outer wall 212 having an interior surface 214, the interior surface 214 defining primary lumen 216 extending longitudinally between the exit port 218 of distal end 202 of cannula 200 and the proximal hub end 206 of cannula 200. The primary lumen 216 provides fluid communication between exit port 218, and proximal hub end 206 for delivery of fluid to the central venous system. In use, exit port 218 is in fluid communication with the central venous system, preferably disposed within, or at least approximately within, the superior vena cava. Exit port 218 is comprised, for example, of a hole at distal end 202.

Catheter apparatus 10g is designed for prolonged disposition within the patient to facilitate long term delivery of fluid to the circulatory system. As a result, the subcutaneous tissue surrounding cannula 200 tends to become swollen, infected, and painful. Consequently, catheter apparatus 10g further comprises delivery means for delivering fluid medicament, such as an anesthetic agent (not shown), to essentially only the area of subcutaneous tissue surrounding portion 204 of cannula 200.

One example of the delivery means, for example, comprises: (i) secondary lumen 222, shown in FIGS. 20 and 21, formed in outer wall 212 along at least a portion of cannula 200; and (ii) means for communicating fluid medicament to essentially only the area of subcutaneous tissue surrounding cannula 200. In one embodiment the means for communicating fluid medicament to essentially only the area of subcutaneous tissue surrounding cannula 200 comprises means, in fluid communication with the secondary lumen 222, for communicating fluid medicament from the secondary lumen 222 to essentially only the area of subcutaneous tissue surrounding cannula portion 204. In one embodiment, the means for communicating fluid medicament to essentially only the area of subcutaneous tissue surrounding cannula 200 extends into, but not essentially beyond the subcutaneous tissue of the chest wall when indwelling distal end 202 is positioned within the superior vena cava.

Examples of the secondary lumen 222 will be discussed in detail below. In another embodiment, rather than a secondary lumen, the delivery means comprises means for defining an interior lumen, as discussed above.

Optionally, apparatus 10g further comprises a tertiary lumen 223, shown in FIG. 20, formed in outer wall 212 along at least a portion of cannula 200 in fluid communication with the central venous system through exit port 225 for delivering fluid, such as a fluid different from that in the primary lumen 216, to the central venous system. Different lumens may be employed to deliver chemically non-compatible fluids. As shown in FIG. 21, tertiary lumen 223 preferably comprises at least one longitudinal bore formed through the outer wall, the at least one longitudinal bore being substantially parallel to the primary lumen 216.

In a preferred embodiment, exit port 218 is disposed distally with respect to exit port 225. This staggering of exit ports 218, 225 assists the user in preventing mixing of fluids before the fluids reach the circulatory system. One skilled in the art will recognize that additional lumens may be added to catheter 10g, depending upon the amount and variety of fluids desired to be delivered.

Examples of the secondary lumen 222 will now be discussed in more detail. As shown in FIGS. 20 and 21, the secondary lumen 222 comprises at least one longitudinal bore formed in the outer wall 212, the at least one longitudinal bore being substantially parallel to the primary lumen 216. The at least one longitudinal bore may comprise a variety of shapes, as shown in the various embodiments of FIGS. 21 through 21d.

Figure 21A:
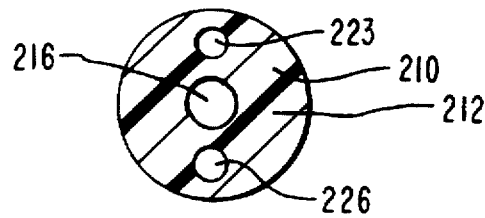
FIG. 21a is cross-sectional view of an alternate catheter apparatus for providing fluid to a patient's circulatory system.
Figure 21B:
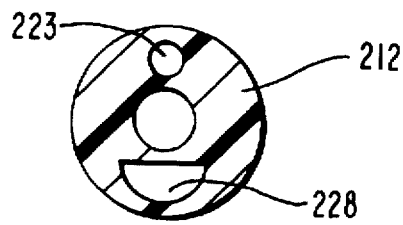
FIG. 21b is cross-sectional view of an alternate catheter apparatus for providing fluid to a patient's circulatory system.
Figure 21C:
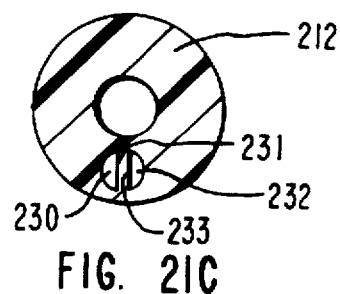
FIG. 21c cross-sectional view of an alternate catheter apparatus for providing id to a patient's circulatory system.

For example, the at least one longitudinal bore may be a U-shaped bore 224, when viewed in transverse cross section, as shown in FIG. 21. In another embodiment, as shown in FIG. 21a, a single, circular shaped longitudinal bore 226 is employed. The at least one longitudinal bore may be a D-shaped longitudinal bore 228, as shown in FIG. 21b. As shown in FIG. 21c, in yet another embodiment, both the secondary and tertiary lumens comprise D-shaped longitudinal bores, 230, 232, respectively, the respective flat sides 231, 233 of bores 230, 232 adjacent and parallel to each other.

Figure 21D:
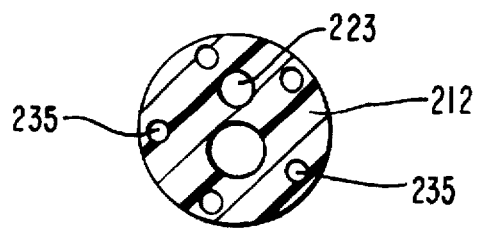
FIG. 21d cross-sectional view of an alternate catheter apparatus for providing fluid to a patient's circulatory system.

Optionally, as shown in FIG. 21d, the secondary lumen may also comprise a plurality of longitudinal bores 235 formed through the outer wall, each bore in fluid communication with a central hub, such as discussed above and in U.S. patent application entitled "Catheter Apparatus with Means for Subcutaneous Delivery of Anesthetic Agent or Other Fluid Medicament," Filed on Mar. 22, 1996, Ser. No. 08/622,458, which is incorporated herein in its entirety by reference. In one embodiment, the central hub comprises tube 239 shown in FIG. 19 comprising a single tube which branches into a variety of tubes, each of which is in fluid communication with a corresponding longitudinal bore 235. In another embodiment, the central hub comprises a fluid reservoir in fluid communication with infusion ports such as holes in bores 235. In each of the embodiments featured in FIGS. 21–21d, each longitudinal bore is substantially parallel to primary lumen 216.

In one embodiment, the means for communicating fluid medicament to essentially only the area of subcutaneous tissue surrounding cannula 200 comprises at least one delivery hole 234 or slit, or a plurality of holes or slits, located between the markers 208 and 220 formed in outer wall 210 and in fluid communication with secondary lumen 222 for providing a fluid communication path between the secondary lumen 222 and the surrounding subcutaneous tissue for the fluid medicament. As is shown in FIG. 20, in one embodiment, each hole 234 extends completely through the cylindrical wall 212 of cannula 200 so as to provide fluid communication with secondary lumen 222.

It will be appreciated that the means for communicating fluid medicament to essentially only the area of subcutaneous tissue surrounding cannula 200 may be comprised of a variety of equivalent structures such as those discussed above in previous embodiments and others which may be employed in the present invention.

In one embodiment, catheter 10g includes a single delivery hole 234. As one option, in this embodiment, cannula 200 is inserted into the stoma such that the delivery hole 234 is on the top of the catheter, allowing fluid to flow downwardly therefrom around the circumference of cannula 200, thus using the force of gravity to dispel the fluid medicament throughout the stoma. In this embodiment, it is preferred to place a mark on the catheter to indicate that the cannula should be inserted with a certain end up.

Typically the chest wall or other subcutaneous track acts as a sealed cavity. This sealed cavity creates a wicking action, distributing medicament longitudinally and about the exterior surface 209 of cannula 200 throughout the stoma to the surrounding subcutaneous tissue. Because of this wicking action, even a single hole 234 from a circular shaped lumen 226, is an efficient, effective secondary lumen for providing fluid medicament to the surrounding subcutaneous tissue.

In another embodiment, a plurality of delivery holes or slits are spaced along cannula 200 to insure that anesthetizing agent is evenly and uniformly delivered to the surrounding chest wall. For example, in the U-shaped embodiment of FIG. 21, the multiple longitudinal bore embodiment of 21d, and the D-shaped embodiment of FIG. 21b, it is possible to place a plurality of holes 234 across a significant portion of the circumference of the catheter, as shown in FIG. 19, thereby distributing fluid evenly within the stoma to the subcutaneous tissue.

The U-shaped embodiment of FIG. 21 and the D-shaped embodiment of FIG. 21b are efficient to manufacture and feature increased surface area for disposition of holes 234 therethrough, ensuring delivery of medicament to a broader area. The single longitudinal bore 226 of FIG. 21a is efficient to manufacture and is not readily collapsible. The embodiment of FIG. 21c provides an efficient design in which lumens 230, 232 are stable, not readily collapsed and use space efficiently. The multiple lumen embodiment of FIG. 21d permits the delivery of fluid along almost the entire circumference of cannula 200 and features stable lumens 235 which do not readily collapse.

As shown in FIG. 19, in one embodiment, holes 234 are offset from each other in a checkerboard orientation. Each hole is spaced in a diagonal relationship with the neighboring hole, promoting distribution of fluid medicament. This angled, diagonal relationship is available when employing the embodiments of FIGS. 21, 21b, and 21d and allows for an efficient use of space.

FIGS. 19 and 20 illustrate how the primary, secondary, and tertiary lumens 216, 222, 223 can be joined in fluid communication with respective primary, secondary, and tertiary infusion ports 236, 238, 240. For example, hub means, such as hub 244 comprises a primary passageway means, such as primary hub lumen 246, in fluid communication with primary lumen 216, for communicating nutrients from primary infusion port 236 and primary infusion tube 237 to the primary lumen 216. In addition, hub 244 comprises a secondary passageway means, such as secondary hub lumen 248, for communicating fluid medicament from a secondary infusion port 238 and a secondary infusion tube 239 to the secondary lumen 222. In addition, hub 244 comprises a tertiary passageway means, such as tertiary hub lumen 250 in fluid communication with tertiary lumen 223 for communicating fluid from a tertiary infusion port 240 and a tertiary infusion tube 241 to the tertiary lumen 223.

In one embodiment, ports 236, 238, and 240 and hub 244 are placed in fluid communication with cannula 200 following insertion of cannula 200 through the subcutaneous tissue. In one embodiment, catheter 10g comprises a tear apart cannula, allowing the insertion of cannula 200 through the subcutaneous tissue, but also allowing separation of tubes 237, 239, and 241. In another embodiment, tubes 236, 238, and 240 are integrally attached in fluid communication with primary, secondary and tertiary lumens 216, 222, and 223, respectively, and the hub is not joined in fluid communication with the lumens or tubes. Instead, the hub serves as a cover, surrounding the junction between the tubes and lumens.

In one embodiment, delivery holes 234 not only allow the fluid medicament to be communicated from the secondary lumen 222 to the subcutaneous tissue, but also allow bodily fluids to enter the secondary lumen 222 and tube 239, thereby allowing a practitioner to monitor fluid flow through a translucent or transparent tube 239. When fluid under pressure is exerted out of the holes 234, significant amounts of bodily fluids will not be allowed to enter the holes 234 because of the high velocity of spray. Hydrostatic pressure on the secondary lumen 222 may thus be used to prevent bodily fluid from entering cannula 200.

It will be appreciated that the fluid medicament employed in various embodiments of this invention may be a variety of anesthetics, antibiotics, anti-inflamatories or other anti-infection medicaments, including, for example, lidocaine.

In a preferred embodiment, a cuff made of a fabric material is disposed within the opaque markers 208, 220, thereby providing an additional barrier to bacteria. In one embodiment, the fabric cuff is made of DACRON, which promotes bacterial ingrowth, stabilizing the catheter and acting as a physical barrier to bacteria. Another fabric cuff which may be employed in conjunction or separately from the DACRON cuff is known as a VITA CUFF, which includes absorbent material impregnated with silver ions which leach out over time, preventing bacterial growth.

As another embodiment of a delivery means, catheter apparatus 10g comprises a sheath means, such as one of the various embodiments discussed above, the sheath means designed for placement between cannula 200 and the subcutaneous tissue in the chest wall. Examples of the sheath means include integral sheaths and selectively attachable and detachable sheaths, as discussed above.

In one embodiment, the sheath means comprises a sleeve. For delivery of fluid medicament, in one embodiment, the sleeve includes a secondary lumen formed in the outer wall of the sleeve, such as a plurality of longitudinal bores as discussed above and in U.S. patent application Ser. No. 08/622,458, filed Mar. 22, 1996, incorporated previously herein by reference. In another embodiment, the sleeve includes a means for defining an interior lumen, examples of which are as discussed above.

To deliver fluid medicament to the interior or secondary lumen, the sheath means further includes a hub means, as discussed above. The sleeve further includes means for communicating fluid medicament from the interior or secondary lumen to essentially only area of the subcutaneous tissue surrounding the sheath means.

It will be appreciated that, in one embodiment, the sheath means is disposed between cannula 200 and the subcutaneous tissue in the chest wall, for example, after cannula 200 has been inserted into the chest wall. The hub means preferably remains outside of the body and the distal end of the sheath means is disposed within the chest wall. In one embodiment, the distal end of the sheath means is positioned adjacent marker 208, while the proximal end of the sheath means protrudes from the body adjacent hub 244.

In one embodiment the sheath means is positioned on cannula 200 so that a means for communicating fluid medicament from the secondary or interior lumen to essentially only the area of subcutaneous tissue surrounding the sheath means, such as at least one delivery hole or slit, or a plurality of holes or slits, is disposed about the portion 204 of cannula 200 surrounded by the subcutaneous tissue of the chest wall.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by U.S. Patent is:

1. An indwelling catheter apparatus for providing fluid to a patient's central venous system, comprising:

an indwelling cannula adapted for insertion through subcutaneous tissue of a patient's chest wall, the indwelling cannula having (i) an indwelling distal end adapted for placement approximately within the superior vena cava, the distal end having an exit port in fluid communication with the patient's central venous system, (ii) a proximal hub end adapted for positioning outside of the body, and (iii) a primary lumen providing fluid communication between the proximal hub end and the exit port for delivery of fluid to the central venous system; and delivery means for delivering fluid medicament to essentially only the area of subcutaneous tissue surrounding the cannula.

2. An indwelling catheter apparatus as defined in claim 1, wherein the delivery means comprises means for communicating fluid medicament to essentially only the area of subcutaneous tissue surrounding the cannula, the means for communicating fluid medicament to essentially only the area of subcutaneous tissue extending into, but not essentially beyond, the area of subcutaneous tissue of the chest wall when the indwelling distal end is positioned within the superior vena cava.

3. An indwelling catheter apparatus as defined in claim 1, wherein the delivery means comprises a secondary lumen formed along at least a portion of the cannula.

4. An indwelling catheter apparatus as defined in claim 3, wherein the secondary lumen comprises at least one longitudinal bore formed in an outer wall of the cannula, the at least one longitudinal bore being substantially parallel to the primary lumen, the bore configured in a U-shape when viewed in a transverse cross section.

5. An indwelling catheter apparatus as defined in claim 3, wherein the secondary lumen comprises at least one longitudinal bore formed in an outer wall of the cannula, the at least one longitudinal bore being substantially parallel to the primary lumen, the bore configured in a D-shape when viewed in a transverse cross section.

6. An indwelling catheter apparatus as defined in claim 3, wherein the delivery means comprises at least one delivery hole formed in an outer wall of the cannula and in fluid communication with the secondary lumen, the at least one delivery hole providing a fluid communication path between the secondary lumen and the surrounding chest wall for the fluid medicament.

7. An indwelling catheter as in claim 6, further comprising proximal and distal orienting means for orienting a portion of the catheter apparatus within the subcutaneous tissue, the at least one delivery hole disposed between the proximal and distal orienting means.

8. An indwelling catheter apparatus as defined in claim 3, wherein the delivery means comprises at least one slit formed in an outer wall of the cannula and in fluid communication with the secondary lumen, the at least one slit providing a fluid communication path between the secondary lumen and the surrounding chest wall for the fluid medicament.

9. An indwelling catheter apparatus as defined in claim 3, wherein the delivery means comprises a plurality of delivery holes formed in an outer wall of the cannula, each delivery hole providing a fluid communication path between the secondary lumen and the surrounding chest wall for the fluid medicament.

10. An indwelling catheter apparatus as defined in claim 9, wherein neighboring delivery holes are offset from each other in a diagonal relationship, promoting distribution of fluid medicament.

11. An indwelling catheter apparatus as defined in claim 1, further comprising a tertiary lumen formed along at least a portion of the cannula for providing fluid to the superior vena cava, the tertiary lumen being substantially parallel to the primary lumen.

12. An indwelling catheter apparatus as defined in claim 1, wherein the delivery means comprises a sheath means disposed about a portion of the cannula.

13. An indwelling catheter apparatus for providing fluid to a patient's central venous system, comprising:

an indwelling cannula adapted for insertion through subcutaneous tissue of a patient's chest wall, the indwelling cannula having (i) an indwelling distal end, the distal end having an exit port in fluid communication with the superior vena cava; and (ii) a proximal hub end adapted for positioning outside of the body, the cannula comprising a cylindrical tube, the cylindrical tube having a cylindrical outer wall having an interior surface, the interior surface defining a primary lumen extending longitudinally between the exit port of the cannula and the proximal hub end of the cannula;

a secondary lumen formed in said outer wall along at least a portion of the cannula;

means in fluid communication with the secondary lumen for communicating fluid medicament from the secondary lumen to essentially only the area of subcutaneous tissue surrounding a portion of the cannula; and a tertiary lumen formed in said outer wall along at least a portion of the cannula for providing fluid to the superior vena cava, the tertiary lumen being substantially parallel to the primary lumen.

14. An indwelling catheter apparatus as in claim 13, wherein the secondary lumen comprises a plurality of longitudinal bores formed through the outer wall.

15. An indwelling catheter apparatus as defined in claim 13, wherein the secondary lumen comprises at least one longitudinal bore formed in the outer wall, the at least one longitudinal bore being substantially parallel to the primary lumen, the bore configured in a D-shape when viewed in a transverse cross section;

the tertiary lumen comprises at least one longitudinal bore formed in the outer wall, the at least one longitudinal bore being substantially parallel to the primary lumen, the bore configured in a D-shape when viewed in a transverse cross section; and the secondary and tertiary lumens each have a flat side, the respective flat sides adjacent and parallel to each other.

16. An indwelling catheter apparatus as defined in claim 13, wherein the means in fluid communication with the secondary lumen for communicating fluid medicament from the secondary lumen to essentially only the area of subcutaneous tissue surrounding a portion of the cannula comprises at least one delivery hole, the at least one delivery hole providing a fluid communication path between the secondary lumen and the surrounding chest wall for the fluid medicament.

17. An indwelling catheter apparatus as in claim 13, wherein the primary lumen extends further in a distal direction than the tertiary lumen, separating the fluid delivered by the primary lumen from the fluid delivered by the tertiary lumen.

18. An indwelling catheter as in claim 13, further comprising proximal and distal orienting means for orienting a portion of the catheter apparatus within the subcutaneous tissue.

19. An indwelling catheter apparatus for providing fluid to a patient's central venous system, comprising:

an indwelling cannula adapted for insertion through subcutaneous tissue of a patient's chest wall, the indwelling cannula having (i) an indwelling distal end, the distal end having an exit port disposed within the superior vena cava; and (ii) a proximal hub end adapted for positioning outside of the body, the cannula comprising a cylindrical tube, the cylindrical tube having a cylindrical outer wall having an interior surface, the interior surface defining a primary lumen extending longitudinally between the distal end of the cannula and the proximal hub end of the cannula, the primary lumen in fluid communication with the exit port such that fluid is delivered through the primary lumen into the superior vena cava;

a secondary lumen formed in said outer wall along at least a portion of the cannula, the secondary lumen comprising at least one longitudinal bore formed through the outer wall, the at least one longitudinal bore being substantially parallel to the primary lumen;

a tertiary lumen formed in the outer wall along at least a portion of the cannula, the tertiary lumen comprising at least one longitudinal bore formed through the outer wall, the at least one longitudinal bore being substantially parallel to the primary lumen; and at least one delivery hole providing a fluid communication path between the secondary lumen and the chest wall surrounding the cannula for delivering fluid medicament to essentially only the area of subcutaneous tissue within the chest wall; wherein the primary lumens extends further in a distal direction than the tertiary lumen, separating the fluid delivered by the primary lumen from the fluid delivered by the tertiary lumen.

20. An indwelling catheter apparatus for providing fluid to a patient's circulatory system, comprising:

an indwelling cannula adapted for insertion approximately within a patient's vein and subcutaneous tissue adjacent the vein, the indwelling cannula having (i) an indwelling distal end, the distal end having an exit port in fluid communication with the patient's circulatory system; (ii) a proximal hub end adapted for positioning outside of the body; and (iii) a primary lumen providing fluid communication between the exit port and the proximal hub end for delivery of fluid to the patient's circulatory system;

delivery means for delivering fluid medicament to essentially only the area of subcutaneous tissue surrounding the cannula.

21. An indwelling catheter apparatus as in claim 20, wherein the cannula is an indwelling cannula adapted for insertion through a patient's chest wall and approximately within the superior vena cava for providing fluid to a patient's central venous system.

* * * * *

UNITED STATES PATENT AND TRADEMARK OFFICE
CERTIFICATE OF CORRECTION

PATENT NO. : 5,817,072

DATED : October 6, 1998  Page 1 of 2

INVENTOR(S) : Lampropoulos, et al

It is certified that error appears in the above-identified patent and that said Letters Patent is hereby corrected as shown below:

On the Title Page, fourth line down, after "AGENT" delete "OF" and insert ---- OR ----
On the Title Page, Item [56], 2nd column, line 5, "Roseberg" should read ----- Rosenberg ----
On the Title Page, Item [56], 2nd column, line 7, "Melder" should read ----- Melker -----.

Col. 5, line 37, after "providing" change "id" to --fluid--

Col. 7, line 60, after "slits" change "28" to --48--

Col. 9, line 12, after "comprises" delete an "a"

Col. 9, line 19, after "cannula" change "22" to --14--

Col. 10, line 49, before "present" insert --the--

Col. 14, line 13, after "cannula" change "22" to --14--

UNITED STATES PATENT AND TRADEMARK OFFICE
CERTIFICATE OF CORRECTION

PATENT NO. : 5,817,072

DATED : October 6, 1998           Page 2 of 2

INVENTOR(S) : Lampropoulos, et al

It is certified that error appears in the above-identified patent and that said Letters Patent is hereby corrected as shown below:

Col. 16, line 29, make "Referring" the beginning of a new paragraph.

Col. 17, line 23, after "means" delete ",for example,"

Col. 19, lines 54-55, after "tubes" change "236, 238, and 240" to --237, 239, and 241--

Signed and Sealed this

Third Day of April, 2001

*Attest:*

NICHOLAS P. GODICI

*Attesting Officer*     *Acting Director of the United States Patent and Trademark Office*